US008865895B2

(12) United States Patent
Doutova et al.

(10) Patent No.: US 8,865,895 B2

(45) Date of Patent: *Oct. 21, 2014

(54) ORGANIC COMPOUND, ANISOTROPIC OPTICAL FILM AND METHOD OF PRODUCTION THEREOF

(75) Inventors: Tatyana Doutova, Moscow (RU); Pavel I. Lazarev, London (GB); Elena N. Sidorenko, Moscow (RU)

(73) Assignee: Crysoptix K.K., Tokyo (JP)

(*) Notice: Subject to any disclaimer, the term of this patent is extended or adjusted under 35 U.S.C. 154(b) by 1675 days.

This patent is subject to a terminal disclaimer.

(21) Appl. No.: 12/160,404

(22) PCT Filed: Jan. 15, 2007

(86) PCT No.: PCT/GB2007/000101

§ 371 (c)(1), (2), (4) Date: Oct. 7, 2009

(87) PCT Pub. No.: WO2007/080419

PCT Pub. Date: Jul. 19, 2007

(65) Prior Publication Data

US 2010/0039705 A1 Feb. 18, 2010

(30) Foreign Application Priority Data

Jan. 13, 2006 (GB) .................................. 0600764.5

(51) Int. Cl.

*C07D 487/04* (2006.01)
*C09K 19/32* (2006.01)
*G02B 5/30* (2006.01)
*G02F 1/13363* (2006.01)

(52) U.S. Cl.

CPC ............ *C07D 487/04* (2013.01); *G02B 5/3083* (2013.01); *G02F 2001/133633* (2013.01); *G02F 1/133634* (2013.01); *G02B 5/30* (2013.01)

USPC ............ 544/247; 349/96; 349/117; 349/118; 428/1.31

(58) Field of Classification Search

USPC ............ 349/96, 117, 118; 428/1.31; 544/247

See application file for complete search history.

(56) References Cited

U.S. PATENT DOCUMENTS

| | | | | |
|---|---|---|---|---|
| 5,739,296 | A | 4/1998 | Gvon et al. | |
| 6,174,394 | B1 | 1/2001 | Gvon et al. | |
| 7,888,505 | B2 * | 2/2011 | Doutova et al. | 544/247 |
| 7,889,297 | B2 * | 2/2011 | Palto | 349/118 |
| 8,081,270 | B2 * | 12/2011 | Lazarev | 349/62 |
| 8,142,863 | B2 * | 3/2012 | Palto | 428/1.1 |
| 8,416,376 | B2 * | 4/2013 | Palto | 349/117 |
| 2004/0028839 | A1 * | 2/2004 | Paukshto et al. | 428/1.1 |
| 2004/0058091 | A1 | 3/2004 | Dutova et al. | |
| 2004/0233528 | A1 | 11/2004 | Lazarev et al. | |
| 2006/0062932 | A1 | 3/2006 | Dutova et al. | |

FOREIGN PATENT DOCUMENTS

| | | | |
|---|---|---|---|
| EP | 0961138 | A1 | 12/1991 |
| WO | 2004/003599 | A2 | 1/2004 |

OTHER PUBLICATIONS

Bahadur, "Liquid Crystals—Applications and Uses," vol. 1, p. 101, World Scientific, Singapore—New York, 1990.

Nazarov et al., "Electronic Spectra of Aqueous Solutions and Films Made of Liquid Crystal Ink for Thin Film Polarizers," Molecular Materials, 2001, vol. 14, No. 2, pp. 153-163.

Remizov et al., "Rheology of the Lyotropic Liquid Crystalline Material for Thin Film Polarizers," Molecular Materials, 2001, vol. 14, No. 2, pp. 179-190.

Lydon, "Chromonics," Handbook of Liquid Crystals,1998, vol. 2B, p. 981-1007, Wiley VCH, Weinheim.

Lazarev et al., "Thin Crystal Film Retarders," Proceeding of the 7th International Display Workshops, Materials and Components, Nov. 29-Dec. 1, 2000, Kobe, Japan, pp. 1159-1160.

Fiske et al., "Molecular Alignment in Crystal Polarizers and Retarders," Society for Information Display Int. Symp., Digest of Technical Papers, May 19-24, 2002, Boston, MA, pp. 866-869.

PCT, International Search Report and Written Opinion of the International Searching Authority in PCT/GB2007/000101, May 15, 2007, 10 pages.

* cited by examiner

*Primary Examiner* — Callie Shosho
*Assistant Examiner* — John Freeman
(74) *Attorney, Agent, or Firm* — Whiting IP Law; Adam K. Whiting

(57) ABSTRACT

The present invention is related to 6,7-dihydrobenzimidazo [1,2-c]quinazolin-6-one derivatives of the general structural formula (I), where X is a carboxylic group COOH, m is 0, 1, 2 or 3; Y is a sulfonic group $SO_3H$, n is 0, 1, 2 or 3; Z is an acid amide group L-$NH_2$; p is 0, 1, 2 or 3; K is a counterion selected from the list comprising $H^+$, $NH_4^+$, $Na^+$, $K^+$, $Li^+$, $Mg^{2+}$, $Ca^{2+}$, $Zn^{2+}$, and $Al^{3+}$; s is the number of counterions providing neutral state of the molecule; R is a substituent selected from the list comprising $CH_3$, $C_2H_5$, $NO_2$, Cl, Br, F, $CF_3$, CN, OH, $OCH_3$, $OC_2H_5$, $OCOCH_3$, OCN, SCN, $NH_2$, and $NHCOCH_3$; w is 0, 1, 2, 3 or 4; and $R_1$ is a substituent selected from the list comprising H, $CH_3$, $C_2H_5$, $C_3H_7$, i-$C_3H_7$, $CH_2CH_2CH_2CH_3$, $CH(CH_3)CH_2CH_3$, $CH_2CH(CH_3)CH_3$ and $C(CH_3)_3$ and L is a linking group.

(I)

N, N, N, O, $R_1$, $X_m$, $Y_n$, $Z_p$, $R_w$, $K_s$

49 Claims, 5 Drawing Sheets

ORGANIC COMPOUND, ANISOTROPIC OPTICAL FILM AND METHOD OF PRODUCTION THEREOF

The present invention relates generally to the field of organic chemistry and particularly to organic anisotropic optical films with phase-retarding properties for displays. More specifically, the present invention is related to the synthesis of 6,7-dihydrobenzimidazo[1,2-c]quinazolin-6-one derivatives and the manufacture of anisotropic optical films based on these compounds.

In connection with polarization, compensation and retardation layers, films, or plates described in the present application, the following definitions of terms are used throughout the text.

The definition of a "thin" optical film is related to the wavelength of light: a thin optical film is that having a thickness comparable with a half of the wavelength of light in the working interval of optical spectrum.

The term optical axis refers to a direction in which the propagating light does not exhibit birefringence. The optical properties of an optical compensation film are described by the refractive index ellipsoid, with the refractive indices nx, ny, and nz in the directions of x, y and z axes, respectively. The in-plane x and y axes are mutually orthogonal and are both orthogonal to the vertical z axis.

Liquid crystals are widely used in electronics as optical display elements. In such display systems, a liquid crystal cell is typically situated between a pair of polarizer and analyzer plates. The incident light is polarized by the polarizer and transmitted through a liquid crystal cell, where it is affected by the molecular orientation of the liquid crystal that can be controlled by applying a bias voltage across the cell. Then, the thus altered light passes through the second (output) polarizer that is called analyzer. By employing this scheme, the transmission of light from any external source, including ambient light, can be controlled. The energy required to provide for this control is generally much lower than that required for controlling the emission from luminescent materials used in other types of displays such as cathode ray tubes (CRTs). Accordingly, liquid crystal technology is used in a number of electronic imaging devices, including (but not limited to) digital watches, calculators, portable computers, and electronic games, for which small weight, low power consumption, and long working life are important.

The contrast, colour reproduction (colour rendering), and stable grey scale intensity gradation are important quality characteristics of electronic displays employing liquid crystal technology. The primary factor determining the contrast of a liquid crystal display (LCD) is the propensity for light to "leak" through liquid crystal elements or cells, which are in the dark or "black" pixel state. In addition, the optical leakage and, hence, the contrast of an LCD also depend on the direction from which the display screen is viewed. Typically, the optimum contrast is observed only within a narrow viewing angle range around the normal ($\alpha$=0) to the display and falls off rapidly as the polar viewing angle $\alpha$ is increased. The viewing direction herein is defined as a set of the polar viewing angle ($\alpha$) and the azimuthal viewing angle ($\beta$) as shown in FIG. 1 with respect to a liquid crystal display 1. The polar viewing angle $\alpha$ is measured from the display normal direction 2 and the azimuthal viewing angle $\beta$ spans between an appropriate reference direction 3 in the plane of the display surface 4 and the projection 5 of viewing arrow 6 onto the display surface 4. Various display image properties such as the contrast ratio, color reproduction, and image brightness are functions of the angles $\alpha$ and $\beta$. In colour displays, the leakage problem not only decreases the contrast but also causes colour or hue shifts with the resulting degradation of colour reproduction.

LCDs are now replacing CRTs as monitors for television (TV) sets, computers (especially in notebook computers and desktop computers), central control units, and various devices, for example, gambling machines, electro-optical displays, (e.g., in watches, pocket calculators, electronic pocket games), portable data banks (such as personal digital assistants or mobile telephones). It is expected that the proportion of LCD television monitors with a larger screen size will also sharply increase in the nearest future. However, unless problems related to the effect of viewing angle on the colour reproduction, contrast degradation, and brightness inversion are solved, the replacement of traditional CRTs by LCDs will be limited.

The type of optical compensation required depends on the type of display used in each particular system. In a normally black display, the twisted nematic cell is placed between polarizers whose transmission axes are parallel to one another and to the orientation of the liquid crystal director at the rear surface of the cell (i.e., at the cell side that is away from the viewer). In the unenergized state (zero applied voltage), normally incident light from the backlight system is polarized by the first polarizer and transmitted through the cell with the polarization direction rotated by the twist angle of the cell. The twist angle is set to 90 DEG so that the output polarizer (analyzer) blocks this light. Patterns can be written in the display by selectively applying a voltage to the portions of the display that are to appear illuminated.

However, when viewed at large angles, the dark (unenergized) areas of a normally black display will appear bright because of the angle-dependent retardation effect for the light rays passing through the liquid crystal layer at such angles, whereby off-normal incident light exhibits an angle-dependent change in the polarization. The contrast can be restored by using a compensating element, which has an optical symmetry similar to that of a twist cell but produces the reverse effect. One method consists in introducing an active liquid crystal layer containing a twist cell of the reverse helicity. Another method is to use one or more uniaxial compensators. These compensation methods work because the compensation element has the same optical symmetry as that of the twist nematic cell: both are made of uniaxial birefringent materials having an extraordinary axis that is orthogonal to the normal light propagation direction. These approaches to compensation have been widely utilized because of readily available materials with the required optical symmetry.

Thus, the technological progress poses the task of developing optical elements based on new materials with desired controllable properties. In particular, important optical elements in modern visual display systems are optically anisotropic films with optical characteristics optimised for use in a particular display module.

Various polymeric materials are known in the prior art, which are intended for use in the production of optically anisotropic films. Films based on these polymers acquire optical anisotropy through uniaxial extension and coloration with organic or inorganic (iodine) dyes. Poly(vinyl alcohol) (PVA) is among polymers that are widely used for this purpose. However, a relatively low thermal stability of PVA based films limits their applications. PVA based films are described in greater detail in the monograph *Liquid Crystals—Applications and Uses*, B. Bahadur (ed.), World Scientific, Singapore—New York (1990), Vol. 1, p. 101.

Organic dichroic dyes constitute a new class of materials currently gaining prominence in the manufacture of optically anisotropic films with desirable optical and working characteristics. Films based on these materials can be obtained by applying an aqueous liquid crystal (LC) solution of supramolecules containing dye molecules onto a substrate surface, with the subsequent evaporation of water.

A hydrophobic-hydrophilic balance of molecules of polycyclic organic compounds makes them soluble in water and stimulates their self-assembly into supramolecules. Organic compounds in water form a colloid system or lyotropic liquid crystal, where molecules aggregate into supramolecules and these supramolecules represent kinetic units of the colloidal system (see, P. I. Lazarev, M. V. Paukshto, "Multilayer optical coating," U.S. 2004/0233528 (2004)). Spectral characteristics and rheological properties of materials (see, V. Nazarov, L. Ignatov, K. Kienskaya, "Electronic Spectra of Aqueous Solutions and Films Made of Liquid Crystal Ink for Thin Film Polarizers," *Molecular Materials*, Vol. 14, No. 2, pp. 153-163 (2001); S. Remizov, A. Krivoshchepov, V. Nazarov, A. Grodsky, "Rheology of The Lyotropic Liquid Crystalline Material for Thin Film Polarizers," *Molecular Materials*, Vol. 14, No. 2, pp. 179-190 (2001)) indicate strong tendency of these molecules to aggregate, even in diluted aqueous solutions, with formation of supramolecules with columnar structure. Columnar structure is specific for flat shaped molecules grouped in "face-to-face" fashion with hydrophobic molecular planar cores of aromatic conjugated bond system stacked on each other inside of the supramolecule core and the hydrophilic peripheral groups exposed to water. Water provides the medium for electrostatic interaction and mutual alignment of supramolecules with resulting lyotropic liquid crystal structure of certain symmetry at certain level of aggregates concentration. Formation of supramolecules starts at low concentration of amphiphilic compounds in the water. There are two types of data that can be used as a basis for previous statement which are (1) optical spectra of molecular compounds that are building block of supramolecules, and (2) light scattering data that correlate with size of aggregates that are present in the system.

The applied films are rendered anisotropic either by preliminary mechanical orientation of the substrate surface or by post-treatment using external mechanical, electromagnetic, or other orienting forces applied to the LC film material on the substrate.

Liquid crystal properties of dye solutions are well known. In recent years, use of liquid crystals based of such dye solutions for commercial applications such as LCDs and glazing coatings has received much attention.

Dye supramolecules form lyotropic liquid crystals (LLCs). Substantial molecular ordering or organization of dye molecules in the form of columns allows such supramolecular LC mesophases to be used for obtaining oriented, strongly dichroic films.

Dye molecules forming supramolecular LC mesophases possess unique properties. These dye molecules contain functional groups located at the periphery, which render these molecules soluble in water. Organic dye mesophases are characterized by specific structures, phase diagrams, optical properties, and solubility as described in greater detail in: J. Lydon, Chromonics, in *Handbook of Liquid Crystals*, Wiley VCH, Weinheim (1998), Vol. 2B, p. 981-1007 (see also references therein).

Anisotropic films characterized by high optical anisotropy can be formed from LLC systems based on dichroic dyes. Such films exhibit the properties of so-called E-type polarizers (due to the absorption of light by supramolecular complexes). Organic conjugated compounds with the general molecular structure similar to that of dye molecules, but exhibiting no absorption in the visible spectral range, can be used as retarders and compensators.

Retarders and compensators are the films possessing phase-retarding properties in the spectral regions where the optical absorption is absent. The phase-retarding or compensating properties of such films are determined by their double refraction also known as birefringence (Δn):

$$\Delta n=|n_o-n_e|,$$

which is the difference of the refractive indices for the extraordinary wave ($n_e$) and the ordinary wave ($n_o$). The $n_e$ and $n_o$ values vary depending on the orientation of molecules in a medium and on the direction of light propagation. For example, if this direction coincides with the optical or crystallographic axis, the ordinary polarization is predominantly observed. If the light propagates in the perpendicular direction or at some angle to the optical axis, the light emerging from the medium will separate into extraordinary and ordinary components.

It is also important to note that, in addition to the unique optical properties, the films based on organic aromatic compounds are characterized by a high thermal stability and radiation resistance (photostability).

Extensive investigations aimed at the development of new methods for fabricating dye-based films through variation of the film deposition conditions have been described in U.S. Pat. Nos. 5,739,296 and 6,174,394 and in published patent application EP 961138. Of particular interest is the development of new compositions of lyotropic liquid crystals by introducing modifying, stabilizing, surfactant and/or other additives in the known compositions, which improve the characteristics of LC films.

There is increasing demand for anisotropic films with improved selectivity in various wavelength ranges. Films exhibiting different optical absorption maxima over a wide spectral interval ranging from infrared (IR) to ultraviolet (UV) regions are required for a variety of technological applications. Hence, much recent research attention has been directed to the synthesis of new materials for the manufacture of isotropic and/or anisotropic birefringent films, polarizers, retarders or compensators (herein collectively referred to as optical materials or films) for LCD and telecommunication applications, such as (but not limited to) those described in P. Yeh, *Optical Waves in Layered Media*, New York, John Wiley & Sons (1998) and in P. Yeh and C. Gu, *Optics of Liquid Crystal Displays*, New York, John Wiley & Sons, (1999).

It has been found that ultrathin birefringent films can be fabricated using the known methods and technologies developed for the production of optically anisotropic films based on organic dye LLC systems. For example, the manufacture of thin, optically anisotropic crystalline films based on disulfoacids of the red dye Vat Red 14 has been described by P. Lazarev and M. Paukshto, Thin Crystal Film Retarders (in: *Proceeding of the 7th International Display Workshops, Materials and Components*, Kobe, Japan, Nov. 29-Dec. 1 (2000), pp. 1159-1160) In particular, such films can be obtained using cis- and trans-isomer mixtures of naphthalenetetracarboxylic acid dibenzimidazole:

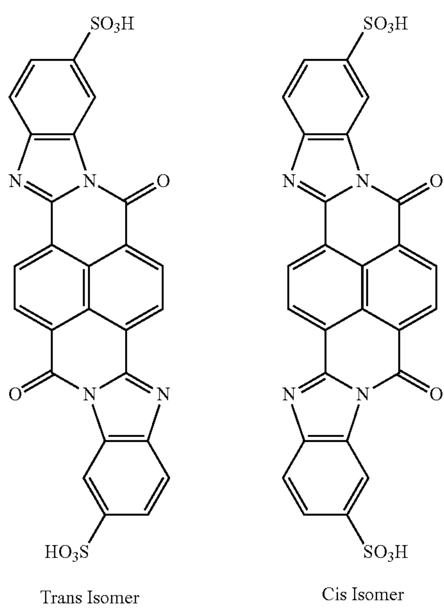 [SMILES: O=c1c2ccc3c4c(ccc(c24)c2nc4ccc(S(=O)(=O)O)cc4n12)c(=O)n1c2cc(S(=O)(=O)O)ccc2nc31 ; O=c1c2ccc3c(=O)n4c5cc(S(=O)(=O)O)ccc5nc4c4ccc(c2c34)c2nc3ccc(S(=O)(=O)O)cc3n12]

Trans Isomer Cis Isomer

This technology makes it possible to control the direction of the crystallographic axis of a film during the deposition and crystallization of LC molecules on a substrate (e.g., on a glass plate). The obtained films have uniform compositions and are characterized by high molecular and/or crystal ordering, with a dichroic ratio of approximately $K_d$~28, which makes them useful optical materials, in particular, for polarizers, retarders, and birefringent films or compensators.

Thin birefringent films transparent in the visible spectral range have been also obtained based on disodium chromoglycate (DSCG):

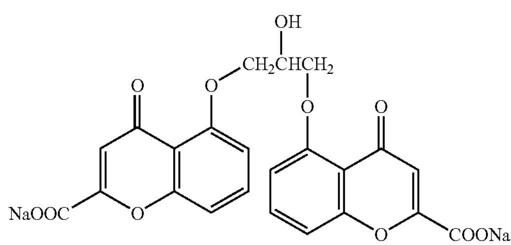

The anisotropy of oriented films made of DSCG is not very high: a difference in the refractive indices Δn is in the visible range is approximately 0.1 to 0.13. However, the thicknesses of films based on DSCG can be varied over a wide range, thus making possible the preparation of films with desired phase-retarding properties despite low specific anisotropy characteristics of the material. These films are considered in greater detail in T. Fiske et al., Molecular Alignment in *Crystal Polarizers and Retarders: Society for Information Display Int. Symp*. (Boston, Mass., May 19-24 (2002), *Digest of Technical Papers*), pp. 566-569. The main disadvantage of many of these films is their dynamic instability, which leads to gradual recrystallization of the LC molecules and the resulting degradation of the optical anisotropy.

Other anisotropic film materials, based on water-soluble organic dyes, have been also obtained using the aforementioned technology; see, for example, U.S. Pat. Nos. 5,739,296 and 6,174,394 and European patent EP 0961138. However, such materials exhibit high optical absorption in the visible spectral range, which limits their use in applications requiring transparent birefringent films.

Still other anisotropic materials have been synthesized based on acenaphtho[1,2-b]quinoxaline sulfoderivatives having the general structural formula

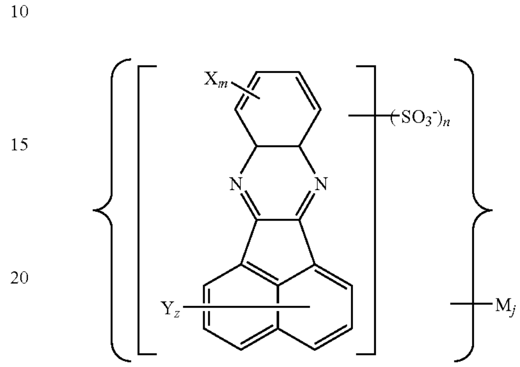

where n is an integer in the range from 1 to 4; m is an integer in the range from 0 to 4; z is an integer in the range from 0 to 6; m+z+n≤10; X and Y are molecular fragments individually selected from the list including $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$; M is a counter ion; and j is the number of counter ions in the molecule; with a proviso that, when n=1 and $SO_3$— occupies position 1, then m≠0 or z≠0.

Thus, there is a general need for films, which are optically anisotropic and sufficiently transparent in the spectral regions in which they are intended to operate. In particular, there is a need for such optical films transparent in the visible spectral range. It is therefore desirable to provide improved methods for the synthesis and manufacture of optically anisotropic films. It is also desirable to provide optical films resistant to humidity and temperature variations.

In a first aspect, the present invention provides a 6,7-dihydrobenzimidazo[1,2-c]quinazolin-6-one derivative of the general structural formula (I)

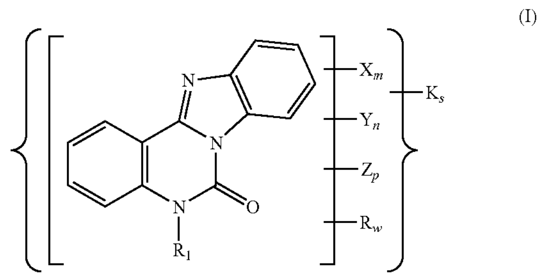

where X is a carboxylic group COOH, m is 0, 1, 2 or 3; Y is a sulfonic group $SO_3H$, n is 0, 1, 2 or 3; Z is an acid amide group $L\text{-}NH_2$; p is an integer in the range from 0, 1, 2 or 3; K is a counterion selected from the list comprising $H^+$, $NH_4^+$, $Na^+$, $K^+$, $Li^+$, $Mg^{2+}$, $Ca^{2+}$, $Zn^{2+}$ and $Al^{3+}$; s is the number of counterions providing neutral state of the molecule; R is a substituent selected from the list comprising $CH_3$, $C_2H_5$, $NO_2$, Cl, Br, F, $CF_3$, CN, OH, $OCH_3$, $OC_2H_5$, $OCOCH_3$, OCN, SCN, $NH_2$, and $NHCOCH_3$; w is 0, 1, 2, 3 or 4; $R_1$ is a substituent selected from the list comprising H, $CH_3$, $C_2H_5$, $C_3H_7$, i-$C_3H_7$, $CH_2CH_2CH_2CH_3$, $CH(CH_3)CH_2CH_3$, $CH_2CH(CH_3)CH_3$ and $C(CH_3)_3$ and L is a linking group. The values of at least two of said integers m, n and p are not equal to 0 and said derivative consequently comprises at least two different groups selected from the list comprising X, Y, and Z. Said 6,7-dihydrobenzimidazo[1,2-c]quinazolin-6-one derivative does not substantially absorb incident electromagnetic radiation in the visible spectral range. In the present invention the visible range is considered as the wavelength range with a lower boundary of approximately 400 nm, and an upper boundary of approximately 700 nm. It is also supposed that the upper boundary of UV spectral range is approximately equal or lower that the lower boundary of the visible range.

In a second aspect, the present invention provides an anisotropic optical film comprising a substrate having front and rear surfaces, and at least one organic layer applied on the front surface of the substrate and comprising at least one 6,7-dihydrobenzimidazo[1,2-c]quinazolin-6-one derivative with the general structural formula (I)

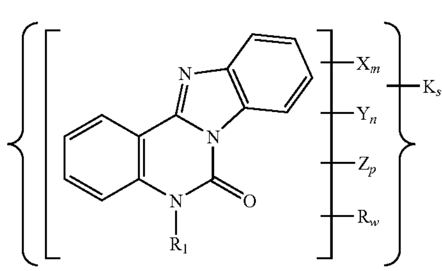

where X is a carboxylic group COOH, m is 0, 1, 2 or 3; Y is a sulfonic group $SO_3H$, n is 0, 1, 2 or 3; Z is an acid amide group L-$NH_2$; p is 0, 1, 2 or 3; K is a counterion selected from the list comprising $H^+$, $NH_4^+$, $Na^+$, $K^+$, $Li^+$, $Mg^{2+}$, $Ca^{2+}$, $Zn^{2+}$, $Al^{3+}$ and $Ba^{2+}$, s is the number of counterions providing neutral state of the molecule; R is a substituent selected from the list comprising $CH_3$, $C_2H_5$, $NO_2$, Cl, Br, F, $CF_3$, CN, OH, $OCH_3$, $OC_2H_5$, $OCOCH_3$, OCN, SCN, $NH_2$, and $NHCOCH_3$; w is 0, 1, 2, 3 or 4; $R_1$ is a substituent selected from the list comprising H, $CH_3$, $C_2H_5$, $C_3H_7$, i-$C_3H_7$, $CH_2CH_2CH_2CH_3$, $CH(CH_3)CH_2CH_3$, $CH_2CH(CH_3)CH_3$ and $C(CH_3)_3$ and L is a linking group. The values of at least two of said integers m, n and p are not equal to 0 and said derivative comprises at least two different groups selected from the list comprising X, Y, and Z. Said organic layer does not substantially absorb incident electromagnetic radiation in the visible spectral range. The anisotropic optical film may be an anisotropic optical crystal film.

In a third aspect, the present invention provides a method of manufacturing anisotropic optical films comprising the following steps: (a) depositing an aqueous solution of supramolecules, formed from one or more 6,7-dihydrobenzimidazo[1,2-c]quinazolin-6-one derivatives on a substrate, and (b) drying said aqueous solution of supramolecules to form a solid layer. Said 6,7-dihydrobenzimidazo[1,2-c]quinazolin-6-one derivative has the general structural formula (I)

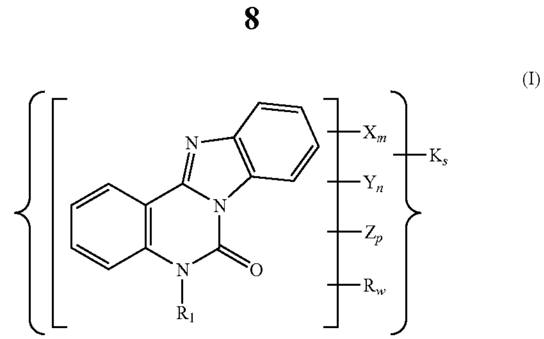

where X is a carboxylic group COOH, m is 0, 1, 2 or 3; Y is a sulfonic group $SO_3H$, n is 0, 1, 2 or 3; Z is an acid amide group L-$NH_2$; p is 0, 1, 2 or 3; K is a counterion selected from the list comprising $H^+$, $NH_4^+$, $Na^+$, $K^+$, $Li^+$, $Mg^{2+}$, $Ca^{2+}$, $Zn^{2+}$ and $Al^{3+}$; s is the number of counterions providing neutral state of the molecule; R is a substituent selected from the list comprising $CH_3$, $C_2H_5$, $NO_2$, Cl, Br, F, $CF_3$, CN, OH, $OCH_3$, $OC_2H_5$, $OCOCH_3$, OCN, SCN, $NH_2$, and $NHCOCH_3$; w is 0, 1, 2, 3 or 4; $R_1$ is a substituent selected from the list comprising H, $CH_3$, $C_2H_5$, $C_3H_7$, i-$C_3H_7$, $CH_2CH_2CH_2CH_3$, $CH(CH_3)CH_2CH_3$, $CH_2CH(CH_3)CH_3$ and $C(CH_3)_3$ and L is a linking group. The values of at least two of said integers m, n and p are not equal to 0 and said derivative comprises at least two different groups selected from the list comprising X, Y, and Z. The method of manufacturing an anisotropic optical film may be a method of manufacturing an anisotropic optical crystal film.

The general description of the present invention having been made, a further understanding can be obtained by reference to the specific preferred embodiments, which are given herein only for the purpose of illustration and are not intended to limit the scope of the appended claims.

In its first aspect, the present invention provides 6,7-dihydrobenzimidazo[1,2-c]quinazolin-6-one derivatives of the general structural formula (I)

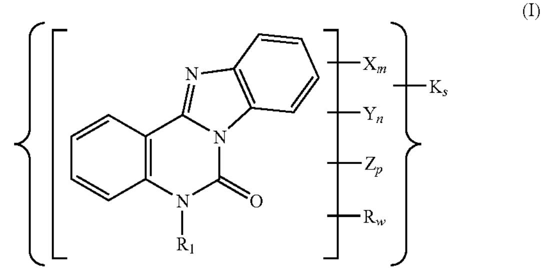

where X is a carboxylic group COOH, m is 0, 1, 2 or 3; Y is a sulfonic group $SO_3H$, n is 0, 1, 2 or 3; Z is an acid amide group L-$NH_2$; p is 0, 1, 2 or 3; K is a counterion selected from the list comprising $H^+$, $NH_4^+$, $Na^+$, $K^+$, $Li^+$, $Mg^{2+}$, $Ca^{2+}$, $Zn^{2+}$ and $Al^{3+}$; s is the number of counterions providing neutral state of the molecule; R is a substituent selected from the list comprising $CH_3$, $C_2H_5$, $NO_2$, Cl, Br, F, $CF_3$, CN, OH, $OCH_3$, $OC_2H_5$, $OCOCH_3$, OCN, SCN, $NH_2$, and $NHCOCH_3$; w is 0, 1, 2, 3 or 4; $R_1$ is a substituent selected from the list comprising H, $CH_3$, $C_2H_5$, $C_3H_7$, i-$C_3H_7$, $CH_2CH_2CH_2CH_3$, $CH(CH_3)CH_2CH_3$, $CH_2CH(CH_3)CH_3$ and $C(CH_3)_3$ and L is a linking group. The values of at least two of said integers m, n and p are not equal to 0 and said derivative comprises at least two different groups selected from the list comprising X, Y, and Z. Said 6,7-dihydrobenzimidazo[1,2-c]quinazolin-6-one derivative does not substantially absorb the incident electromagnetic radiation in the visible spectral range. The number of counterions s may equal zero. In this case the molecule is in the neutral state. The counterion may be selected from the group consisting of $H^{+}$, $NH_{4+}$, $Na^+$, $K^+$, $Li^+$, $Mg^{2+}$, $Ca^{2+}$, $Zn^{2+}$ and $Al^{3+}$ or from the group consisting of $H^+$, $NH_4^+$, $Na^+$, $K^+$, and $Li^+$. L is preferably CO or $SO_2$. In one preferred embodiment of the disclosed invention, the 6,7-dihydrobenzimidazo[1,2-c]quinazolin-6-one derivatives further ensure the absorption of electromagnetic radiation in at least one predetermined wavelength subrange of the UV spectral range. The molecules of such 6,7-dihydrobenzimidazo[1 ;2-c]quinazolin-6-one derivatives can absorb electromagnetic radiation only in a part of the UV spectral range, rather than in the entire range, and this part of the UV range will be called subrange. This subrange can be determined experimentally for each particular 6,7-dihydrobenzimidazo[1,2-c]quinazolin-6-one derivative. In one preferred embodiment of the disclosed 6,7-dihydrobenzimidazo[1,2-c]quinazolin-6-one derivatives, at least one said acid amide group is carboxyamide $CONH_2$. In another preferred embodiment of the disclosed 6,7-dihydrobenzimidazo[1,2-c]quinazolin-6-ones, at least one said acid amide group is sulfonamide $SO_2NH_2$. Examples of 6,7-dihydrobenzimidazo[1,2-c]quinazolin-6-one derivatives comprising at least one carboxylic group COOH, wherein the integer m is between 1 and 3 and said derivative has the general structural formula from the group comprising structures 1 to 11, are given in Table 1.

TABLE 1

Examples of 6,7-dihydrobenzimidazo[1,2-c]quinazolin-6-one derivatives containing carboxylic groups (1)

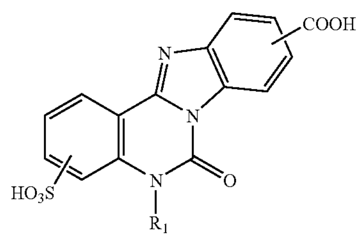

(2)

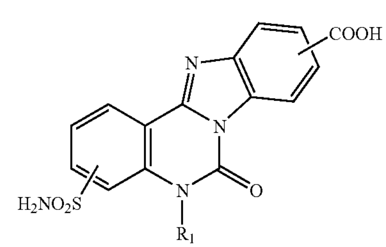

(3)

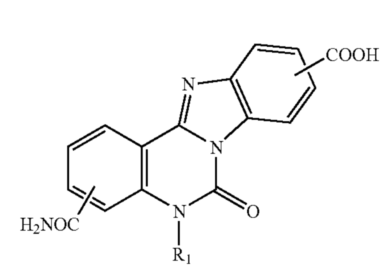

TABLE 1-continued

Examples of 6,7-dihydrobenzimidazo[1,2-c]quinazolin-6-one derivatives containing carboxylic groups (4)

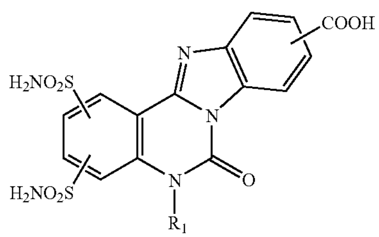

(5)

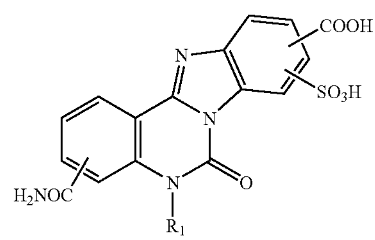

(6)

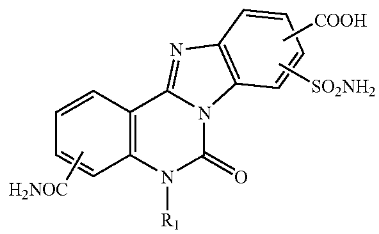

(7)

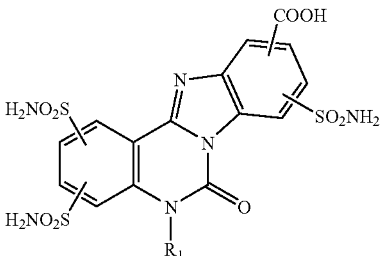

(8)

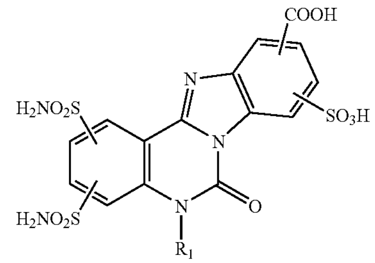

TABLE 1-continued

| Examples of 6,7-dihydrobenzimidazo[1,2-c]quinazolin-6-one derivatives containing carboxylic groups |
|---|

(9)

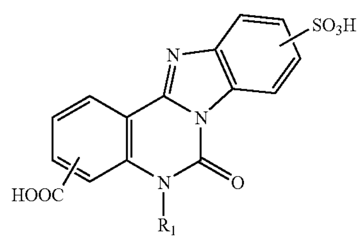

(10)

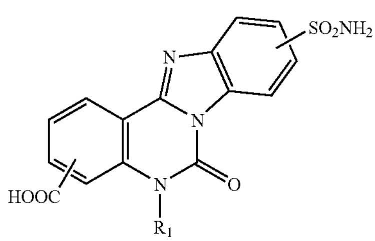

(11)

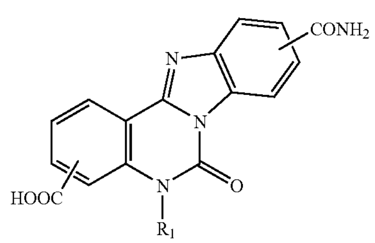

In another preferred embodiment of the disclosed 6,7-dihydrobenzimidazo[1,2-c]quinazolin-6-one derivatives, said acid group, providing solubility in water, is a sulfonic group. Examples of the 6,7-dihydrobenzimidazo[1,2-c]quinazolin-6-one derivatives comprising sulfonic groups $SO_3H$, wherein integer n is between 1 and 3 and said derivative has the general structural formula from the list comprising structures 12 to 20, are given in Table 2.

TABLE 2

| Example of 6,7-dihydrobenzimidazo[1,2-c]quinazolin-6-one derivatives containing sulfonic groups |
|---|

(12)

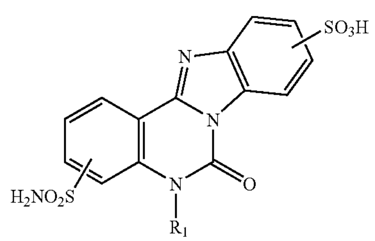

TABLE 2-continued (13)

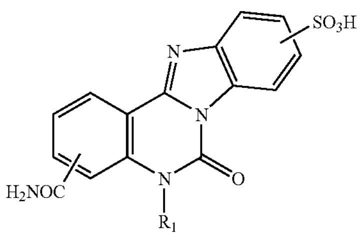

(14)

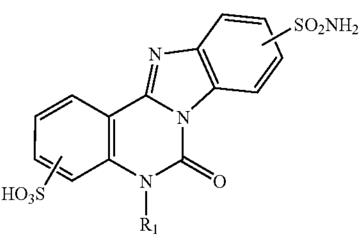

(15)

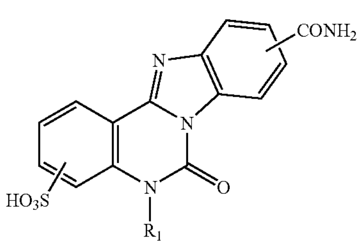

(16)

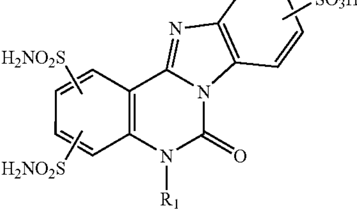

(17)

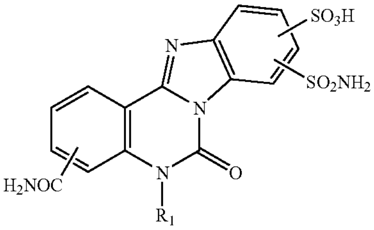

(18)

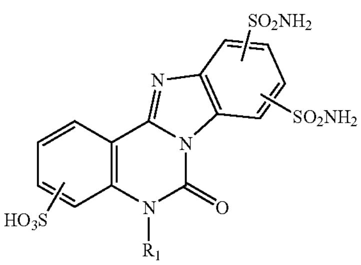

TABLE 2-continued

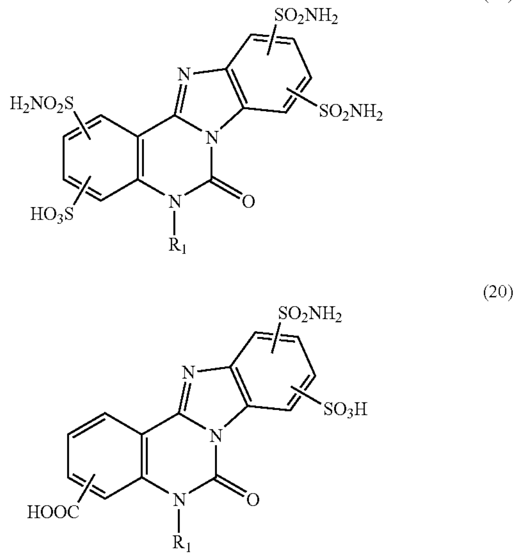

In one preferred embodiment of the present invention, the derivative comprises one or more carboxylic acid groups and one or more sulfonic groups. In another preferred embodiment of the present invention, the derivative comprises one or more carboxylic acid group and one or more sulfonamide groups. In still another preferred embodiment of the present invention, the derivative comprises one or more carboxylic acid groups and one or more carboxyamide groups. In yet another preferred embodiment of the present invention, the derivative comprises one or more sulfonic acid groups and one or more carboxyamide groups. In a possible preferred embodiment of the present invention, the derivative comprises one or more sulfonic acid groups and one or more sulfonamide groups. In another preferred possible embodiment of the present invention, the derivative comprises one or more sulfonic acid groups and one or more sulfonamide groups and one or more carboxyamide groups. In one preferred embodiment of the present invention, the derivative comprises one or more carboxylic acid groups and one or more sulfonamide groups and one or more carboxyamide groups. In another preferred embodiment of the present invention, the derivative comprises one or more carboxylic acid groups and one or more sulfonic acid groups and one or more carboxyamide groups. In still another preferred embodiment of the present invention, the derivative comprises one or more carboxylic acid groups and one or more sulfonic acid groups and one or more sulfonamide groups. In yet another preferred embodiment of the present invention, the derivative comprises one or more carboxylic acid groups and one or more sulfonic acid groups and one or more sulfonamide groups and one or more carboxyamide groups.

Preferred 6,7-dihydrobenzimidazo[1,2-c]quinazolin-6-one derivatives include 2(3)-sulfo-6,7-dihydrobenzimidazo [1,2-c]quinazolin-6-one-9-carboxylic acid; 2(3)-sulfo-6,7-dihydrobenzimidazo[1,2-c]quinazolin-6-one-10-carboxylic acid; 2(3)-sulfonamide-6,7-dihydrobenzimidazo[1,2-c] quinazolin-6-one-9-carboxylic acid; 2(3)-sulfonamide-6,7-dihydrobenzimidazo[1,2-c]quinazolin-6-one-10-carboxylic acid; 2(3)-sulfo6,7-dihydrobenzimidazo[1,2-c]quinazolin-6-one-9-carboxylic acid amide; 2(3)-sulfo-6,7-dihydrobenzimidazo[1,2-c]quinazolin-6-one-10-carboxylic acid amide; and 6,7-dihydrobenzimidazo[1,2-c]quinazolin-6-one sulfosulfonamides.

In its second aspect, the present invention provides an anisotropic optical film comprising a substrate having the front and rear surfaces and at least one organic layer applied on the front surface of the substrate and comprising at least one 6,7-dihydrobenzimidazo[1,2-c]quinazolin-6-one derivative with the general structural formula

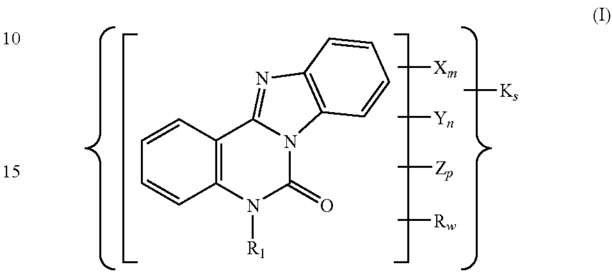

where X is a carboxylic group COOH; m is 0, 1, 2 or 3; Y is a sulfonic group $SO_3H$; n is 0, 1, 2 or 3; Z is an acid amide group L-$NH_2$; p is 0, 1, 2 or 3; K is a counterion selected from the list comprising $H^+$, $NH_4^+$, $Na^+$, $K^+$, $Li^+$, $Mg^{2+}$, $Ca^{2+}$, $Zn^{2+}$, $Al^{3+}$ and $Ba^{2+}$, s is the number of counterions providing neutral state of the molecule; R is a substituent selected from the list comprising $CH_3$, $C_2H_6$, $NO_2$, Cl, Br, F, $CF_3$, CN, OH, $OCH_3$, $OC_2H_5$, $OCOCH_3$, OCN, SCN, $NH_2$, and $NHCOCH_3$; w is 0, 1, 2, 3 or 4; $R_1$ is a substituent selected from the list comprising H, $CH_3$, $C_2H_5$, $C_3H_7$, i-$C_3H_7$, $CH_2CH_2CH_2CH_3$, $CH(CH_3)CH_2CH_3$, $CH_2CH(CH_3)CH_3$ and $C(CH_3)_3$ and L is a linking group. The values of at least two of said integers m, n and p are not equal to 0 and said derivative comprises at least two different groups selected from the list comprising X, Y, and Z. Said organic layer does not substantially absorb incident electromagnetic radiation in the visible spectral range. The counterion may be selected from the group consisting of $H^+$, $NH_4^+$, $Na^+$, $K^+$, $Li^+$, $Mg^{2+}$, $Ca^{2+}$, $Zn^{2+}$, $Ba^{2+}$ and $Al^{3+}$ or from the group consisting of $H^+$, $NH_4^+$, $Na^+$, $K^+$, $Li^+$, $Mg^{2+}$, $Ca^{2+}$, $Zn^{2+}$, $Ba^{2+}$ and $Sr^{2+}$. In one preferred embodiment of the disclosed anisotropic optical film, said organic layer absorbs electromagnetic radiation in at least one predetermined spectral subrange of the UV range. Such anisotropic optical films can absorb electromagnetic radiation only in a part of the UV spectral range, rather than in the entire range, and this part of the UV range is called the subrange. This subrange can be determined experimentally for each particular aqueous solution of an 6,7-dihydrobenzimidazo[1,2-c]quinazolin-6-one derivative used for the formation of the anisotropic optical film. Similarly, the absorption subrange can be experimentally determined for a mixture of 6,7-dihydrobenzimidazo[1,2-c]quinazolin-6-one derivatives used for the formation of said film. Thus, such experimentally determined absorption subrange electromagnetic radiation can be considered as the predetermined subrange.

In one embodiment of the disclosed anisotropic optical film, said organic layer is substantially insoluble in water and/or in water-miscible solvents. The 6,7-dihydrobenzimidazo[1,2-c]quinazolin-6-one derivative used in the anisotropic optical film is preferably as described above with regard to the first aspect of the present invention. Examples of the 6,7-dihydrobenzimidazo[1,2-c]quinazolin-6-one derivative comprising at least one carboxylic group COOH and having the general structural formula from the group comprising structures 1 to 11 are given in Table 1 wherein integer m is between 1 and 3. Examples of the 6,7-dihydrobenzimidazo [1,2-c]quinazolin-6-one derivatives comprising at least one said sulfonic groups $SO_3H$ and having the general structural formula from the group comprising structures 12 to 20 are given in Table 2 wherein integer n is between 1 and 3. In an embodiment of the anisotropic optical film, said organic layer contains two or more 6,7-dihydrobenzimidazo[1,2-c] quinazolin-6-one derivatives with the general structural formula I, each ensuring the absorption of electromagnetic radiation in at least one predetermined wavelength subrange of the UV spectral range. In another embodiment of the anisotropic optical film, said 6,7-dihydrobenzimidazo[1,2-c] quinazolin-6-one derivative forms supramolecules that are oriented predominantly parallel to the substrate surface.

In another preferred embodiment of the anisotropic optical film according to this invention, said organic layer is a biaxial retardation layer that is characterized by two in-plane refractive indices (nx and ny) and one refractive index (nz) in the normal direction. In general case the refractive indices (nx, ny and nz) of biaxial retardation layer have different values.

In one embodiment of the disclosed anisotropic optical film, the refractive indices nx, ny, and nz meet the following condition: $nx<ny<nz$. In still another preferred embodiment of the anisotropic optical film, the in-plane refractive indices (nx and ny) and the organic layer thickness d meet the following condition: $d\cdot(ny-nx)<20$ nm. In one embodiment of the disclosed anisotropic optical film, the in-plane refractive indices (nx and ny) and the organic layer thickness d meet the following condition: $d\cdot(ny-nx)<10$ nm. In still another embodiment of the disclosed anisotropic optical film, the in-plane refractive indices (nx and ny) and the organic layer thickness d meet the following condition: $d\cdot(ny-nx)<5$ nm.

In another embodiment of the disclosed anisotropic optical film, the refractive indices nx, ny, and nz meet the following condition: $nx<nz<ny$. In still another preferred embodiment of the anisotropic optical film, the refractive indices ny and nz and the organic layer thickness d meet the following condition: $d\cdot(ny-nz)<20$ nm. In one embodiment of the disclosed anisotropic optical film, the refractive indices ny and nz and the organic layer thickness d meet the following condition: $d\cdot(ny-nz)<10$ nm. In still another embodiment of the disclosed anisotropic optical film, the refractive indices ny and nz and the organic layer thickness d meet the following condition: $d\cdot(ny-nz)<5$ nm.

It is to be noted that conditions $nx<nz<ny$ are equivalent to $nx>nz>ny$. A refractive index nx is transformed into a refractive index ny when the Cartesian system of coordinates rotates about a vertical axis (Oz-axis) by 90 degrees. Similarly a refractive index ny is transformed into a refractive index nx. In this embodiment, the in-plane refractive indices are not equal among themselves and refractive index in the normal direction has intermediate value between these in-plane refractive indices. This ratio of the refractive indexes disclosed in the invention is invariant relative to a transformation of Cartesian system of coordinates.

In one preferred embodiment of the disclosed anisotropic optical film, the substrate is transparent for electromagnetic radiation in the visible spectral range. In another preferred embodiment of the disclosed anisotropic optical film, said substrate is made of a polymer. In still another preferred embodiment of the disclosed anisotropic optical film, the substrate is made of a glass.

In an embodiment of the disclosed anisotropic optical film, the transmission coefficient of the substrate does not exceed 2% at any wavelength in the UV spectral range. In an embodiment of the disclosed anisotropic optical film, the transmission coefficient of the substrate in the visible spectral range is no less than 90%. In another embodiment of the anisotropic optical film, the rear surface of the substrate is covered with an additional antireflection or antiglare coating. In one preferred embodiment of the disclosed invention, the substrate further comprises a reflective layer that is applied onto the rear surface of the substrate.

In a preferred embodiment of the present invention, the anisotropic optical film further comprises an additional adhesive transparent layer deposited above said reflective layer. In one embodiment of the anisotropic optical film, the substrate is a specular or diffusive reflector. In another embodiment of the anisotropic optical film, the substrate is a reflective polarizer. In still another preferred embodiment, the anisotropic optical film further comprises a planarization layer deposited onto the front surface of the substrate. In yet another preferred embodiment of the invention, the anisotropic optical film further comprises an additional transparent adhesive layer placed on top of the organic layer. In one embodiment of the disclosed invention, the anisotropic optical film further comprises a protective coating formed on the transparent adhesive layer. In one preferred embodiment of the disclosed anisotropic optical film, the transmission coefficient of the adhesive layer does not exceed 2% at any wavelength in the UV spectral range. In another preferred embodiment of the disclosed anisotropic optical film, the transmission coefficient of the adhesive layer in the visible spectral range is no less than 90%. In still another preferred embodiment of the disclosed invention, the anisotropic optical film comprises two or more organic layers, wherein each of these layers contains different 6,7-dihydrobenzimidazo[1,2-c]quinazolin-6-one derivatives with the general structural formula I, ensuring the absorption of electromagnetic radiation in at least one predetermined wavelength subrange of the UV spectral range.

In its third aspect, the present invention provides a method of manufacturing an anisotropic optical film, which comprises the following steps: (a) depositing an aqueous solution of supramolecules, formed from one or more 6,7-dihydrobenzimidazo[1,2-c]quinazolin-6-one derivatives on a substrate, and (b) drying of said aqueous solution of supramolecules to form a solid layer, wherein said 6,7-dihydrobenzimidazo[1, 2-quinazolin-6-one derivative has the general structural formula (I)

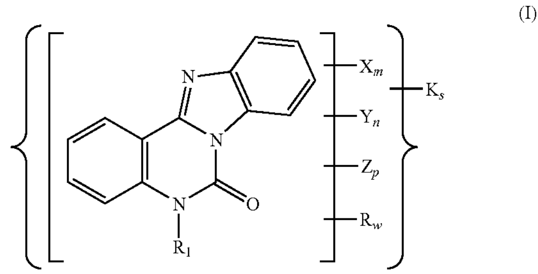

Here, X is a carboxylic group COOH; m is 0, 1, 2 or 3; Y is a sulfonic group $SO_3H$; n is 0, 1, 2 or 3; Z is an acid amide group $L\text{-}NH_2$; p is 0, 1, 2 or 3; K is a counterion selected from the list comprising $H^+$, $NH_4^+$, $Na^+$, $K^+$, $Li^+$, $Mg^{2+}$, $Ca^{2+}$, $Zn^{2+}$ and $Al^{3+}$; s is the number of counterions providing neutral state of the molecule; R is a substituent selected from the list comprising $CH_3$, $C_2H_5$, $NO_2$, Cl, Br, F, $CF_3$, CN, OH, $OCH_3$, $OC_2H_5$, $OCOCH_3$, OCN, SCN, $NH_2$, and $NHCOCH_3$; w is 0, 1, 2, 3 or 4; $R_1$ is a substituent selected from the list comprising H, $CH_3$, $C_2H_5$, $C_3H_7$, i-$C_3H_7$, $CH_2CH_2CH_2CH_3$, $CH(CH_3)CH_2CH_3$, $CH_2CH(CH_3)CH_3$ and $C(CH_3)_3$ and L is a linking group. The values of at least two of said integers m, n and p are not equal to 0 and said derivative comprises at least two different groups selected from the list comprising X, Y, and Z. The counterion may be selected from the group consisting of $H^+$, $NH_4^+$, $Na^+$, $K^+$, $Li^+$, $Mg^{2+}$, $Ca^{2+}$, $Zn^{2+}$, and $Al^{3+}$ or from the group consisting of $H^+$, $NH_{4+}$, $Na^+$, $K^+$ and $Li^+$.

In another preferred embodiment of the invention, the method further includes the application of an external alignment action upon the aqueous solution of supramolecules prior to the drying step.

In still another preferred embodiment of the disclosed method, said aqueous solution also ensures the absorption of electromagnetic radiation in at least one predetermined wavelength subrange of the UV spectral range. Such aqueous solutions absorb electromagnetic radiation only in a part of the UV spectral range, rather than in the entire range, and this part of the UV range is called the subrange. This subrange can be determined experimentally for each particular aqueous solution of an 6,7-dihydrobenzimidazo[1,2-c]quinazolin-6-one derivative used for the formation of the anisotropic optical film. Similarly, the absorption subrange can be experimentally determined for a mixture of 6,7-dihydrobenzimidazo[1,2-c]quinazolin-6-one derivatives used for the formation of said film. Thus, such experimentally determined absorption subrange electromagnetic radiation can be considered as the predetermined subrange.

The 6,7-dihydrobenzimidazo[1,2-c]quinazolin-6-one derivative used in the method of the present invention is preferably as described above with regard to the first aspect of the present invention.

In one embodiment, the acid group, providing solubility in water, is a carboxylic group. Examples of the 6,7-dihydrobenzimidazo[1,2-c]quinazolin-6-one derivatives comprising at least one carboxylic group COOH and having the general structural formula from the group comprising structures 1 to 11 are given in Table 1, wherein integer m is between 1 and 3. In another embodiment, the acid group, providing solubility in water, is a sulfonic group. Examples of the 6,7-dihydrobenzimidazo[1,2-c]quinazolin-6-one derivatives comprising at least one sulfonic group $SO_3H$ and having the general structural formula from the group comprising structures 12 to 20 are given in Table 2 wherein said integer n is between 1 and 3.

In one preferred embodiment of the disclosed method, said aqueous solution is based on a water-miscible solvent. In still another preferred embodiment of the disclosed method, the drying step comprises treatment with an airflow. In yet another preferred embodiment of the disclosed method, the drying step is performed with or without an airflow at an elevated temperature of 23 to 60 degrees centigrade. This temperature range reduces recrystallization and exfoliation (or cracking) of the solid layer. In an embodiment of the disclosed method, the substrate is pretreated so as to provide surface hydrophilization before application of said aqueous solution. In another embodiment of the present invention, the disclosed method further includes treatment of the formed solid layer having the sulfonic groups with a solution of a water-soluble inorganic salt with a $Ba^{2+}$ cation. In one embodiment of the disclosed method, an aqueous solution of supramolecules has a concentration selected from the range between 1% and 35% to produce the film having the predetermined properties. In one embodiment of the disclosed method, the application of said 6,7-dihydrobenzimidazo[1,2-c]quinazolin-6-one derivative solution onto the substrate is accompanied or followed by an external orienting action upon this solution. In yet another preferred embodiment of the disclosed method, the cycle including the technological operations of solution application, alignment action, and drying is repeated two or more times, and sequential solid layers are formed using either the same of different aqueous solutions, which absorb electromagnetic radiation in at least one preset spectral subrange of the UV spectral range.

In one embodiment of the present invention the aqueous solution of supramolecules is a lyotropic liquid crystal solution. In another embodiment of the present invention the aqueous solution of supramolecules is a gel-like solution.

BRIEF DESCRIPTION OF DRAWINGS

Other objects and advantages of the present invention will become apparent upon reading detailed description of the examples and the appended claims provided below, and upon reference to the drawings, in which:

Figure 1:
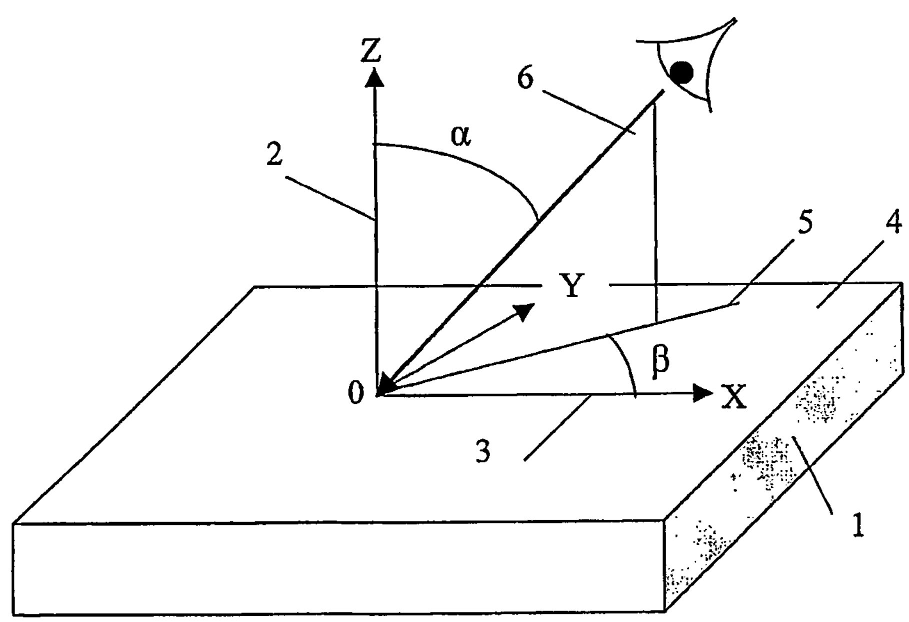
FIG. 1 shows a viewing direction defined as a set of the polar viewing angle $\alpha$ and the azimuthal viewing angle $\beta$.

In order that the invention may be more readily understood, reference is made to the following examples, which are intended to be illustrative of the invention, but are not intended to be limiting in scope. All the abovementioned compounds can be produced by the known ways (sulfonation, sulfochlorination and amidation) from 6,7-dihydrobenzimidazo[1,2-c]quinazoline-6-one and its carboxylic acids. Besides they can be synthesized by the direct condensation of isatin and o-Phenylenediamine substituted with appropriate substituents.

EXAMPLE 1

This example describes the synthesis of a mixture of 2(3)-sulfo-6,7-dihydrobenzimidazo[1,2-c]quinazoline-6-one-9-carboxylic acid and 2(3)-sulfo-6,7-dihydrobenzimidazo[1,2-c]quinazoline-6-one-10-carboxylic acid The first stage is the synthesis of the mixture of 6,7-dihydrobenzimidazo[1,2-c]quinazoline-6-one-9-carboxylic acid and 6,7-dihydrobenzimidazo[1,2-c]quinazoline-6-one-10-carboxylic acid.

3,4-Diaminobenzoic acid (5.0 g) is dissolved in the mixture of water and hydrochloric acid (84.0 g of water and 3.4 g of 35%-solution of HCl) at 20° C. Isatin (4.8 g) is mixed with 70.0 g of glacial acetic acid and 30.0 g of water. The solution of 3,4-diaminobenzoic acid is added to the suspension of isatin and the resulting mixture is stirred for 5 min. Then peroxyacetic acid (6.4 g of 39%) is added. The reaction temperature is raised to 50° C. and the rective mass is kept at this temperature for 20 min, whereupon the temperature is reduced to ambient temperature. Resulting suspension is filtered, the filter cake is washed with diluted acetic acid (50 ml of acetic acid in 100 ml of water). The precipitate is air dried for 15 hours at 100° C. The process yielded 6.6 g of the mixture of 6,7-dihydrobenzimidazo[1,2-c]quinazoline-6-one-9-carboxylic acid and 6,7-dihydrobenzimidazo[1,2-c]quinazoline-6-one-10-carboxylic acid.

The mass spectrum of the product recorded using a Vision 2000 spectrometer is as follows: m/z, 279.3; mol. wt., 279.06. $^1$H NMR (Bruker WM-250, DMSO-$d_6$, δ ppm): 7.39 (q, 2H, 8 Hz); 7.68 (t, 1H, 6 Hz); 7.88 (d, 2H); 8.09 (d, 1H); 8.32 (d, 1H); 8.95 (s, 1H); (isomers mixture). The electronic absorption spectrum of an aqueous solution of the product measured using an Ocean PC 2000 UV/VIS spectrophotometer showed the absorption maxima at $\lambda_{max1}$=325 nm and $\lambda_{max2}$=335-340 nm. The elemental analyses gave the following results (%): C, 64. 52; H, 3. 25; N, 15.05; (anal. calcd. for $C_{15}H_9N_3O_3$); C, 64. 71; H, 3. 13; N, 15.00 (found).

Finally, this example describes the synthesis of the mixture of 2(3)-sulfo-6,7-dihydrobenzimidazo[1,2-c]quinazoline-6-one-9-carboxylic acid and 2(3)-sulfo-6,7-dihydrobenzimidazo[1,2-c]quinazoline-6-one-10 carboxylic acid. A mixture of sulfo-carboxylic acids of 6,7-dihydrobenzimidazo[1,2-c]quinazoline-6-one is synthesized by sulfonation of the mixture of 9- and 10-carboxylic acids of 6,7-dihydrobenzimidazo[1,2-c]quinazoline-6-one. Mixture of 9-and 10-carboxylic acids of 6,7-dihydrobenzimidazo[1,2-c]quinazoline-6-one (5.0 g) is added to 50 ml of 20% oleum and stirred for 1 h at room temperature. The reaction mass is diluted with water (85 ml). The evolved precipitate is filtered and washed with diluted HCl by slurrying (150 ml of 1% HCl×4) and filtered. The precipitate is air dried at 120° C. The process yielded 4.0 g of the mixture of 2(3)-sulfo-6,7-dihydrobenzimidazo[1,2-c]quinazoline-6-one-9-carboxylic acid and 2(3)-sulfo-6,7-dihydrobenzimidazo[1,2-c]quinazoline-6-one-10-carboxylic acid.

The mass spectrum of the product recorded using a Vision 2000 spectrometer is as follows: m/z, 359.4; mol. wt., 359.02. The electronic absorption spectrum of an aqueous solution of the product measured using an Ocean PC 2000 UV/VIS spectrophotometer showed the absorption maxima at $\lambda_{max1}$=325 nm and $\lambda_{max}$=335-340 nm. The elemental analyses gave the following results (%): C, 50.14; H, 2.52; N, 11.69; S, 8.92; (anal. calcd. for $C_{15}H_9N_3O_6S$); C, 50.44; H, 2.54; N, 11.87 (found).

EXAMPLE 2

This example describes the synthesis of a mixture of sulfonamide-carboxylic acids of 6,7-dihydrobenzimidazo[1,2-c]quinazoline-6-one, which is performed according to the following scheme:

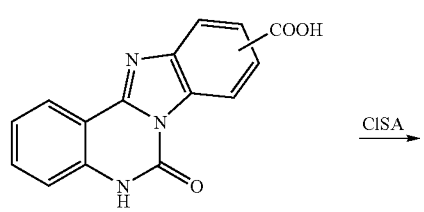

-continued

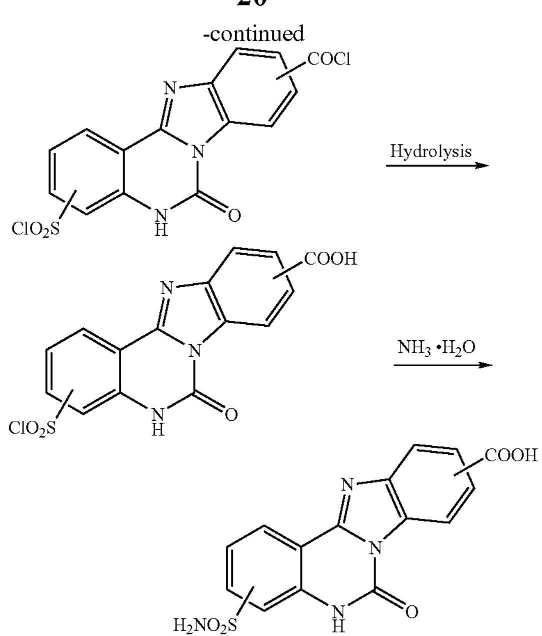

A mixture of 6,7-dihydrobenzimidazo[1,2-c]quinazoline-6-one-9-carboxylic acid and 6,7-dihydrobenzimidazo[1,2-c]quinazoline-6-one-10-carboxylic acid (5.0 g) is stirred with chlorosulfonic acid (50 ml) at 95° C. for 4 hour. Then, the reaction mass is poured into ice (150 g). The precipitate is separated by filtration and washed with ice-cold water (100 ml) until neutral reaction of the wash water. According to HPLC data, the residue on the filter contained 91.5% of the target product and 5% of a carboxysulfonic acid derivative.

This residue is introduced by small portions into aqueous ammonia solution (50 ml), and the mixture is stirred for about one hour at room temperature. Then, the ammonia solution is acidified to pH 2.5 by adding sulfuric acid. The precipitate is filtered, suspended in 3% hydrochloric acid (100 ml), and filtered again. The residue is washed with water (60 ml). This procedure yielded 3.9 g of 2(3)-sulfonamide-6,7-dihydrobenzimidazo[1,2-c]quinazoline-6-one-9-carboxylic acid and 2(3)-sulfonamide-6,7-dihydrobenzimidazo[1,2-c]quinazoline-6-one-10-carboxylic acid mixture (the product comprises 87% of the target compound and 5% of a carboxysulfonic acid derivative). The precipitate is air dried at 105° C.

The mass spectrum of the product recorded using a Vision 2000 spectrometer is as follows: m/z, 358.6; mol. wt., 358.04. The electronic absorption spectrum of an aqueous solution of the product measured using an Ocean PC 2000.UV/VIS spectrophotometer showed the absorption maxima at $\lambda_{max1}$=325 nm and $\lambda_{max2}$=335-340 nm. The elemental analyses gave the following results (%): C, 50.28; H, 2.81; N, 15.64; S, 8.95 (anal. calcd. for $C_{15}H_{10}N_4O_5S$); C, 50.63; H, 2.88; N, 16.01 (found).

EXAMPLE 3

This example describes the synthesis of a mixture of 2(3)-sulfo-6,7-dihydrobenzimidazo[1,2-c]quinazoline-6-one-9-carboxylic acid amide and 2(3)-sulfo-6,7-dihydrobenzimidazo[1,2-c]quinazoline-6-one-10-carboxylic acid amide.

At first, this example describes the synthesis of a mixture of 6,7-dihydrobenzimidazo[1,2-c]quinazoline-6-one-9-carboxylic acid amide and 6,7-dihydrobenzimidazo[1,2-c]

quinazoline-6-one-10-carboxylic acid amide, which is performed according to the following scheme:

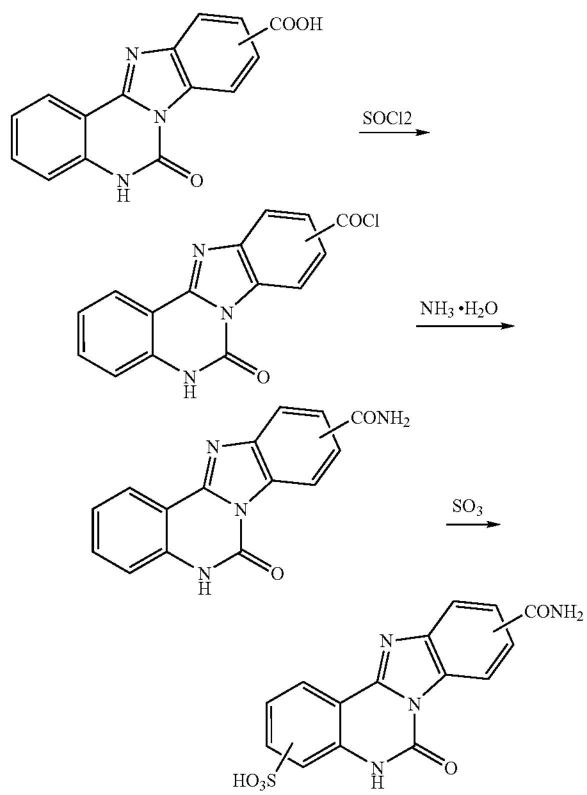

A mixture of 9-carboxy-6,7-dihydrobenzimidazo[1,2-c]quinazolin-6-one (6 g) with thionyl chloride (60 ml) is boiled for 2.5 hours. The final reaction mixture is filtered, and the residue is washed with carbon tetrachloride (50 ml). After vacuum drying, the precipitate is gradually introduced into aqueous ammonia solution (90 ml) with cooling on ice-cold water bath, so that the temperature of the reaction mixture is kept around 5° C. The obtained suspension is stirred for 30 min at the indicated temperature and then heated to 45° C. and stirred at this temperature for 30 min. The precipitate is filtered hot and washed with water (130 ml). The precipitate is air dried at 105° C. This procedure yielded 4.3 g of mixture of 6,7-dihydrobenzimidazo[1,2-c]quinazoline-6-one-9-carboxylic acid amide and 6,7-dihydrobenzimidazo[1,2-c]quinazoline-6-one-10-carboxylic acid amide (the target compound content according to HPLC is 96.0%).

The mass spectrum of the product recorded using a Vision 2000 spectrometer is as follows: m/z, 278.2; mol. wt., 278.08. The electronic absorption spectrum of an aqueous solution of the product measured using an Ocean PC 2000 UV/VIS spectrophotometer showed the absorption maxima at $\lambda_{max1}$=245-250 nm and $\lambda_{max2}$=335-340 nm. The elemental analyses gave the following results (%): C, 64.74; H, 3.62; N, 20.13; (anal. calcd. for $C_{15}H_{10}N_4O_2$); C, 64.53; H, 3.86; N, 20.01 (found).

Finally, this example describes the synthesis of a mixture of 2(3)-sulfo-6,7-dihydrobenzimidazo[1,2-c]quinazoline-6-one-9-carboxylic acid amide and 2(3)-sulfo-6,7-dihydrobenzimidazo[1,2-c]quinazoline-6-one-10-carboxylic acid amide.

A mixture of 6,7-dihydrobenzimidazo[1,2-c]quinazoline-6-one-9-carboxylic acid amide and 6,7-dihydrobenzimidazo[1,2-c]quinazoline-6-one-10-carboxylic acid amide (4.0 g) is stirred with 20% oleum (40 ml) for 1 hour at room temperature. The reaction mass is diluted with water (68 ml) and the precipitate is separated by filtration and washed twice at slurrying with 3% hydrochloric acid (150 ml×2). The precipitate is air dried at 100° C. The procedure yielded 4.2 g of mixture of 2(3)-sulfo-6,7-dihydrobenzimidazo[1,2-c]quinazoline-6-one9-carboxylic acid amide and 2(3)-sulfo-6,7-dihydrobenzimidazo[1,2-c]quinazoline-6-one10-carboxylic acid amide.

The mass spectrum of the product recorded using a Vision 2000 UV/VIS spectrometer (negative ion reflection mode) is as follows: m/z, 358.6; mol. wt., 358.04. The electronic absorption spectrum of an aqueous solution of the product measured using an Ocean PC 2000 UV/VIS spectrophotometer showed the absorption maxima at $\lambda_{max1}$=325 nm and $\lambda_{max2}$=335-340 nm. The elemental analyses gave the following results (%): C, 50.28; H 2.81; N, 15.64; (anal. calcd. for $C_{15}H_{10}N_4O_5S$); C, 49.94; H, 2.93; N, 16.00; (found).

EXAMPLE 4

This example describes the synthesis of a mixture of sulfonamide—sulfonic acids of 6,7-dihydrobenzimidazo[1,2-c]quinazoline-6-one, which is performed according to the following scheme:

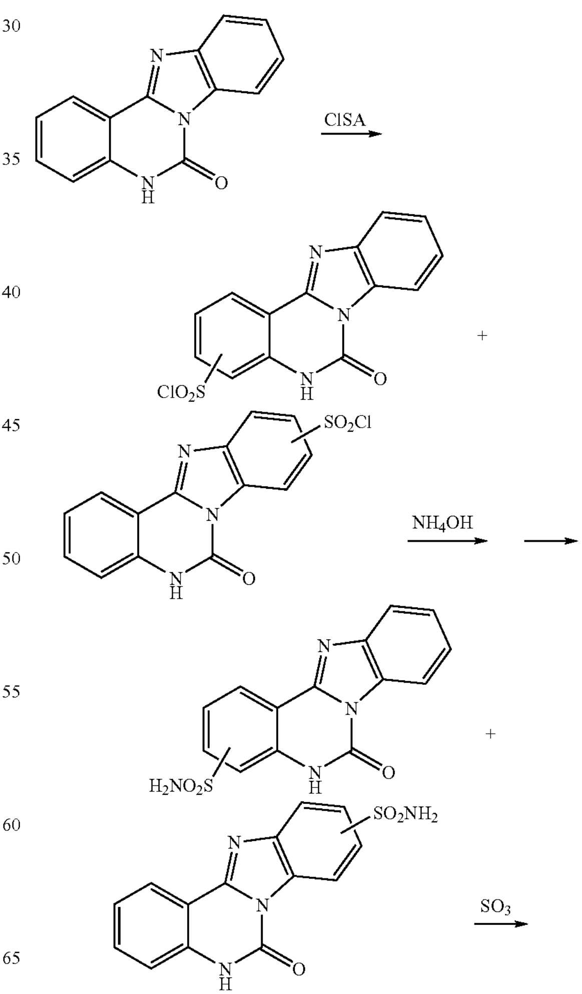

-continued

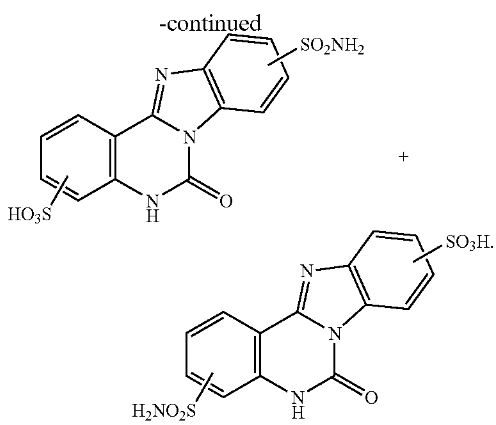

The first stage is the synthesis of a mixture of sulfonamide—sulfonic acids of 6,7-dihydrobenzimidazo[1,2-c]quinazoline-6-one. To this end, a mixture of 6,7-dihydrobenzimidazo[1,2-c]quinazolin-6-one (3 g) and chlorosulfonic acid (18 ml) is stirred for 2 hours at 45-50° C. The reaction mass is poured into ice (100 g). The precipitate is separated by filtration and washed on the filter with ice-cold water (100 ml) until neutral reaction of the wash water. This precipitate is introduced into aqueous ammonia solution (60 ml) and stirred for 30 min at room temperature and then for 30 min at 40° C. Then, the solution is filtered from insoluble contaminations and acidified to pH 6.7with hydrochloric acid. The precipitate is separated by filtration and washed with water (120 ml). The yield of the intermediate sulfonamide mixture is 2.1 g.

Sulfonation of the obtained mixture of 6,7-dihydrobenzimidazo[1,2-c]quinazolin-6-one sulfonamides is carried out as follows. 6,7-Dihydrobenzimidazo[1,2-c]quinazolin-6-one sulfonamides (2 g) were introduced into 20% oleum (12 ml) and the mixture is stirred for one hour at room temperature. The reaction mass is diluted with water (22 ml). The precipitate is filtered and washed twice at slurrying with diluted HCl (30 ml of 3% HCl). Finally, the product is dried in vacuum. This procedure yielded 2 g of the mixture of 6,7-dihydrobenzimidazo[1,2-c]quinazolin-6-one sulfo-sulfonamides.

The mass spectrum of the product recorded using a Vision 2000 spectrometer is as follows: m/z, 394.4; mol. wt., 394.00. The electronic absorption spectrum of an aqueous solution of the product measured using an Ocean PC 2000 UV/VIS spectrophotometer showed the absorption maxima at $\lambda_{max1}$=325 nm and $\lambda_{max2}$=335-340 nm. The elemental analyses gave the following results (%): C, 42.64; H, 2.56; N, 14.21; (anal. calcd. for $C_{14}H_{10}N_4O_6S_2$); C, 42.45; H, 2.93; N, 14.44 (found).

EXAMPLE 5

Figure 2:
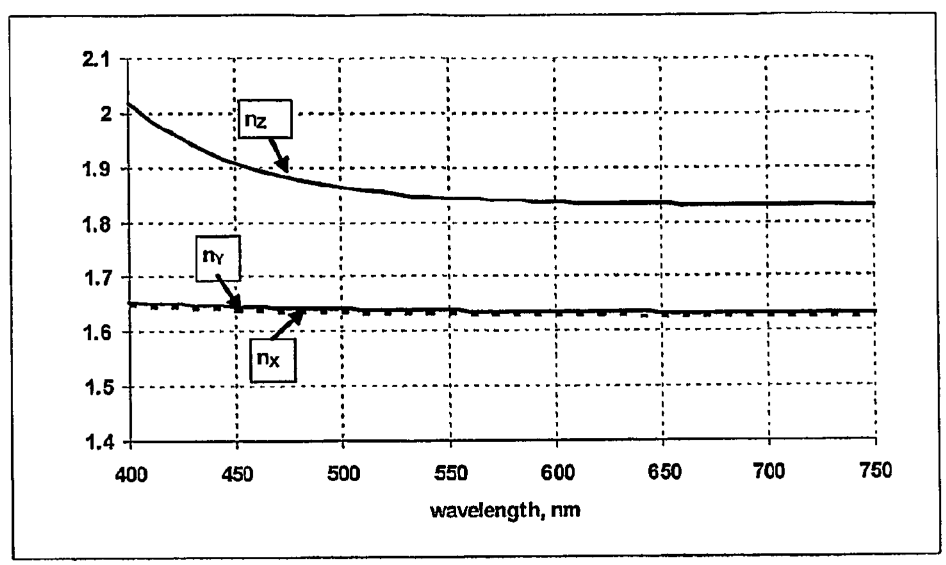
FIG. 2 shows the refractive indices of an organic layer on a glass substrate prepared from a mixture of 6,7-dihydrobenzimidazo[1,2-c]quinazoline-6-one-9-carboxylic acid and 6,7-dihydrobenzimidazo[1,2-c]quinazoline-6-one-10-carboxylic acid having refractive indices nx=1.631, ny=1.637, and nz=1.844 at a wavelength of 550 nm.

This example describes the preparation of an organic layer from a lyotropic liquid crystal solution. A mixture of 6,7-dihydrobenzimidazo[1,2-c]quinazoline-6-one-9-carboxylic acid and 6,7-dihydrobenzimidazo[1,2-c]quinazoline-6-one-10-carboxylic acid (2g) obtained as described in Example 1 is further stirred for 1 hour at a temperature of 20° C. in a mixture of 9.0 ml of deionised water with 2.0 ml of a 10% aqueous ammonia solution until a lyotropic liquid crystal solution is formed. At temperature of 20° C. and relative humidity of 65% the obtained solution is applied onto a pretreated glass plate surface with a Mayer rod #2.5 moved at a linear velocity of 15 mm/s and dries. In order to determine the optical characteristics of the organic layer, the optical transmission spectrum was measured in a wavelength range from 400 to 700 nm using a Cary 500 spectrophotometer. The optical transmission of the organic layer is measured using the light beams linearly polarized parallel and perpendicular to the coating direction ($T_{par}$ and $T_{per}$, respectively). The obtained data were used to calculate the refractive indices (nx, ny, and nz) presented in FIG. 2. The obtained organic layer has refractive indices nx=1.631, ny=1.637, and nz=1.844 at 550 nm wavelength. The measurements showed essentially small values of the absorption coefficients of the organic layer.

EXAMPLE 6

Figure 3:
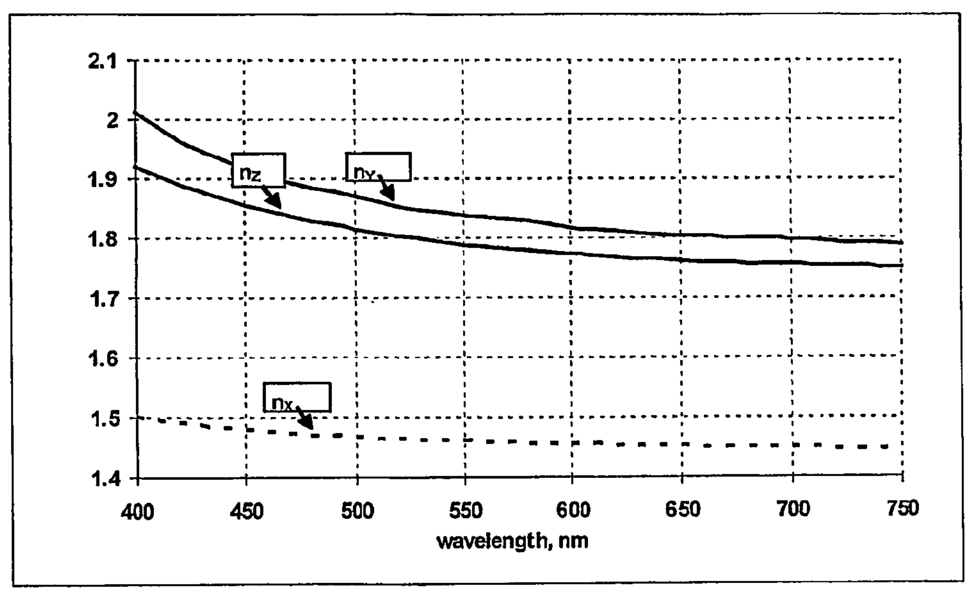
FIG. 3 shows the refractive indices of an organic layer on a glass substrate prepared from a mixture of 2(3)-sulfo-6,7-dihydrobenzimidazo[1,2-c]quinazoline-6-one-9-carboxylic acid and 2(3)-sulfo-6,7-dihydrobenzimidazo[1,2-c]quinazoline-6-one-10 carboxylic acid having refractive indices nx=1.460, ny=1.840, and nz=1.790 at a wavelength of 550 nm.

This example describes the preparation of an organic layer from a lyotropic liquid crystal solution. A mixture of 2(3)-sulfo-6,7-dihydrobenzimidazo[1,2-c]quinazoline-6-one-9-carboxylic acid and 2(3)-sulfo-6,7-dihydrobenzimidazo[1,2-c]quinazoline-6-one-10 carboxylic acid (2 g) obtained as described in Example 1 is stirred for 1 hour at a temperature of 20° C. in a mixture of 9.0 ml of deionised water with 2.0 ml of a 10% aqueous ammonia solution until a lyotropic liquid crystal solution is formed. At temperature of 20° C. and relative humidity of 65% the obtained solution is applied onto a pre-treated glass plate surface with a Mayer rod #2.5 moved at a linear velocity of 15 mm/s and is dried after that. In order to determine the optical characteristics of the organic layer, the optical transmission spectrum is measured in a wavelength range from 400 to 700 nm using a Cary 500 spectrophotometer. The optical transmission of the organic layer is measured using the light beams linearly polarized parallel and perpendicular to the coating direction—$T_{par}$ and $T_{per}$, respectively. The obtained data were used to calculate the refractive indices (nx, ny, and nz) presented in FIG. 3. The obtained organic layer has refractive indices nx=1.460, ny=1.840, and nz=1.790 at 550 nm wavelength. The measurements showed essentially small values of the absorption coefficients of the organic layer.

EXAMPLE 7

Figure 4:
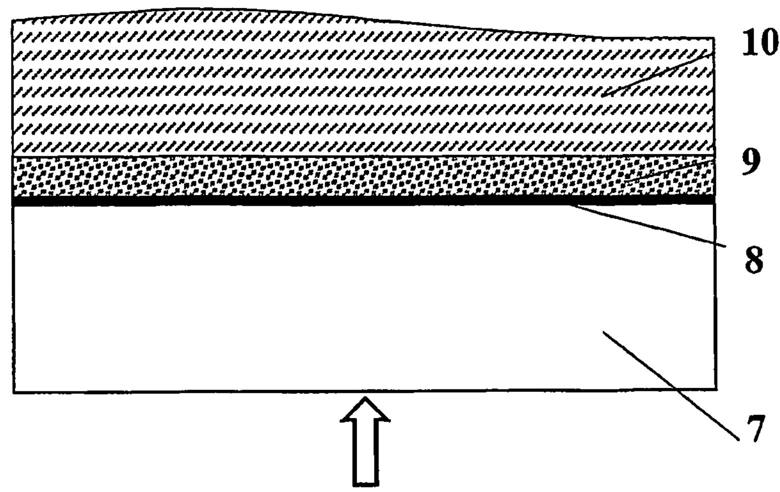
FIG. 4 shows a schematic diagram of the cross section of an anisotropic optical film on a substrate, together with additional adhesive and protective layers.

FIG. 4 shows the cross section of anisotropic an optical film formed on substrate 7. The film comprises organic layer 8, adhesive layer 9, and protective layer 10. Substrate 7 is made of poly(ethylene terephthalate) (PET) (e.g., Toray QT34/QT10/QT40, or Hostaphan 4607, or Dupont Teijin Film MT582). The substrate has a thickness from 30 to 120 μm and a refractive index of n=1.5 (Toray QT10), 1.7 (Hostaphan 4607), 1.51 (Dupont Teijin Film MT582). The organic layer can be manufactured using the methods described in Example 6. The protective layer 10 protects the anisotropic optical film from damage in the course of its transportation. This anisotropic optical film is a semiproduct, which can be used as an external retarder, for example, in LCDs. Upon the removal of protective layer 10, the remaining film is applied onto an LCD glass with adhesive layer 9.

EXAMPLE 8

Figure 5:
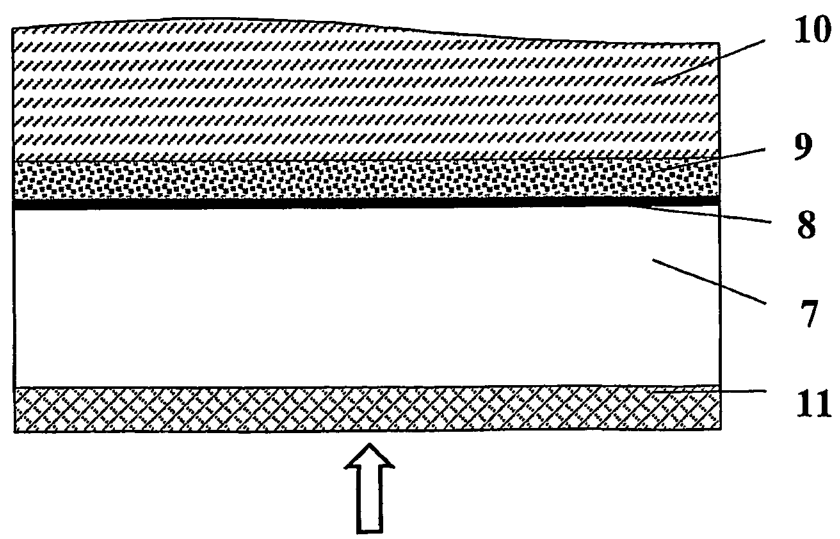
FIG. 5 shows a schematic diagram of the cross section of an anisotropic optical film with an additional antireflection coating.

An anisotropic optical film with an organic layer 11 (FIG. 5) and otherwise identical to the film described above can be applied to the LCD front surface. For example, an antireflection layer of silicon dioxide ($SiO_2$) reduces by 30% the fraction of light reflected from the LCD front surface.

EXAMPLE 9

Figure 6:
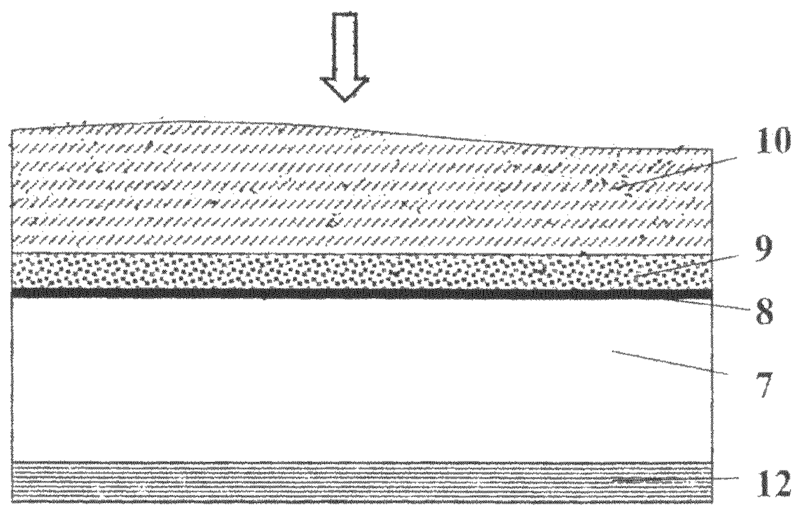
FIG. 6 shows a schematic diagram of the cross section of an anisotropic optical film with an additional reflective layer.

With the above described anisotropic optical film applied to the front surface of an electrooptical device or an LCD, an additional reflective layer 12 can be formed on the rear substrate surface (FIG. 6). The reflective layer can be obtained, for example, by depositing an aluminium film.

EXAMPLE 10

Figure 7:
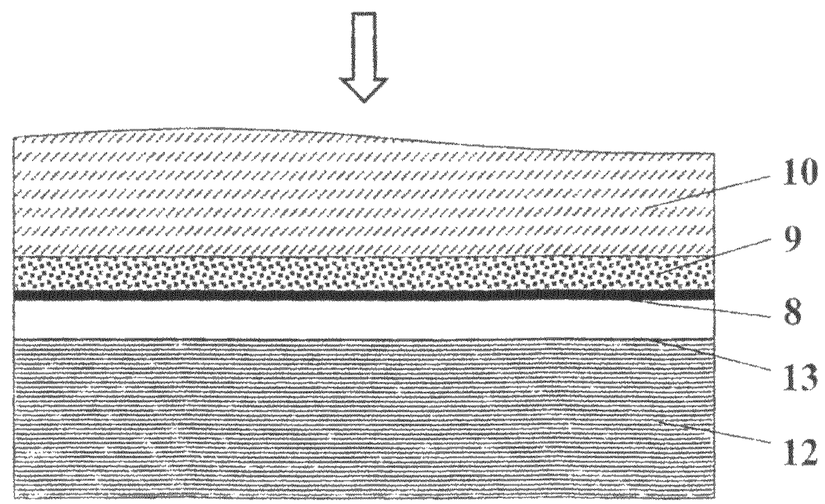
FIG. 7 shows a schematic diagram of the cross section of an anisotropic optical film with a diffuse or specular reflector as the substrate.

FIG. 7 shows the organic layer 8 is applied onto the diffuse or specular semitransparent reflector 12 that serves as a substrate (FIG. 7). The reflector layer 12 may be also covered with planarization layer 13 (optional), which can be made of polyurethane, an acrylic polymer, or any other material. The reflector layer 12 can be made of PET (e.g., Toray QT34/QT10/QT40, Hostaphan 4607, or Dupont Teijin Film MT582). The substrate thickness is 30 to 120 μm and a refractive index is n=1.5 (Toray QT10), 1.7 (Hostaphan 4607), 1.51 (Dupont Teijin Film MT582). The organic layer can be manufactured using the method described in Example 6. The adhesive layer 9 and the protective layer 10 are applied on top of the organic layer.

EXAMPLE 11

This example describes the preparation of an organic layer from a gel-like aqueous solution of supramolecules. A mixture of sulfo-carboxy derivative of 6,7-dihydrobenzimidazo[1,2-c]quinazoline-6-one (1.3 g) obtained as described in Example 1 is stirred for 1 hour at temperature of 40° C. in a mixture of 22.0 ml of deionised water with 1.0 g of anhydrous Zinc oxide plus 2.0 ml of a 10% aqueous sodium hydroxide until a clear solution is formed. The pH of obtained solution (Solution 1) is adjusted by additional amount of 1% aqueous Sodium hydroxide solution. pH level of Solution 1 is set to pH=4.96 value and let sit overnight. After approximately 20 hours, Solution 1 is set to pH level 7.0 by adding a few drops of 1% aqueous Sodium hydroxide solution with simultaneous mixing with use of a magnetic stirrer with a pH-meter electrode immersed into liquid. The obtained solution (Solution 2) is concentrated on a rotary evaporator until concentration of sulfo-carboxy derivative of 6,7-dihydrobenzimidazo[1,2-c]quinazoline-6-one equal to 7% (w/w %) is reached. At temperature of 20° C. and a relative humidity of 65% the obtained solution (Solution 3) is applied onto a pretreated glass plate surface with a Mayer rod #4 moved at a linear velocity of 10 mm/s, and then is dried in an airflow. In order to determine the optical characteristics of the organic layer, the optical transmission spectrum is measured in a wavelength range from 400 to 700 nm using a Cary 500 spectrophotometer. The optical transmission of the organic layer is measured using the light beams linearly polarized parallel and perpendicular to the coating direction—$T_{par}$ and $T_{per}$, respectively. The obtained data were used to calculate the refractive indices (nx, ny, and nz). The obtained organic layer has refractive indices nx=1.495, ny=1.839, and nz=1.841 at a wavelength of 550 nm. The measurements showed essentially small values of the absorption coefficients of the organic layer.

EXAMPLE 12

This example describes the preparation an organic layer from a gel-like aqueous solution of supramolecules. A mixture of sulfo-carboxy derivative of 6,7-dihydrobenzimidazo[1,2-c]quinazoline-6-one (1 g) obtained as described in Example 1 is stirred for 1 hour at temperature of 40° C. in a mixture of 39.0 ml of deionised water with 0.3 g of anhydrous Aluminium chloride plus 2.0 ml of a 10% aqueous sodium hydroxide until a clear solution is formed. The pH of the obtained solution (Solution 1) is controlled by an additional amount of 1% water Sodium hydroxide solution. After 1 hour of mixing, Solution 1 is set to pH level 6.54 by means of adding few drops of 1% aqueous Sodium hydroxide solution while mixed on a magnetic stirrer with a pH-meter electrode immersed into liquid. At temperature of 20° C. and relative humidity of 65% the obtained solution (Solution 2) is applied onto a pretreated glass plate surface with a Mayer rod #4 moved at a linear velocity of 10 mm/s, and is then dried in an airflow. In order to determine the optical characteristics of the organic layer, the optical transmission spectrum is measured in a wavelength range from 400 to 700 nm using a Cary 500 spectrophotometer. The optical transmission of the organic layer is measured using the light beams linearly polarized parallel and perpendicular to the coating direction—$T_{par}$ and $T_{per}$, respectively. The obtained data were used to calculate the refractive indices (nx, ny, and nz). The obtained organic layer has refractive indices nx=1.495, ny=1.655, and nz=1.660 at a wavelength of 550 nm. The measurements showed essentially small values of the absorption coefficients of the organic layer.

The invention claimed is:

1. A 6,7-dihydrobenzimidazo[1,2-c]quinazolin-6-one derivative of the general structural formula I

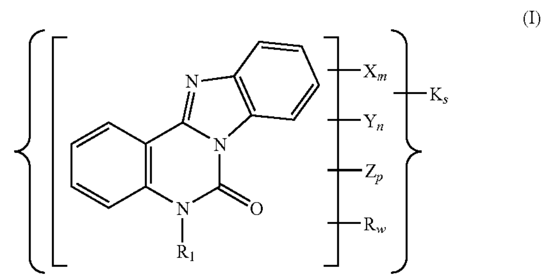

wherein X is a carboxylic group COOH,
- m is 0, 1, 2 or 3;
- Y is a sulfonic group $SO_3H$,
- n is 0, 1, 2 or 3;
- Z is an amide group L-$NH_2$, wherein L is a linking group,
- p is 0, 1, 2 or 3;
- K is a counterion selected from the group consisting of $H^+$, $NH_4^+$, $Na^+$, $K^+$, $Li^+$, $Mg^{2+}$, $Ca^{2+}$, $Zn^{2+}$ and $Al^{3+}$,
- s is the number of counterions providing neutral state of the molecule;
- R is a substituent selected from the group consisting of $CH_3$, $C_2H_5$, $NO_2$, Cl, Br, F, $CF_3$, CN, OH, $OCH_3$, $OC_2H_5$, $OCOCH_3$, OCN, SCN, $NH_2$, and $NHCOCH_3$,
- w is 0, 1, 2, 3 or 4;
- $R_1$ is a substituent selected from the group consisting of H, $CH_3$, $C_2H_5$, $C_3H_7$, i-$C_3H_7$, $CH_2CH_2CH_2CH_3$, $CH(CH_3)CH_2CH_3$, $CH_2CH(CH_3)CH_3$ and $C(CH_3)_3$; and wherein the values of at least two of said integers m, n and p are not equal to 0 and said derivative comprises at least two different groups selected from the list comprising X, Y, and Z; and wherein said derivative does not substantially absorb incident electromagnetic radiation in the visible spectral range.

2. The 6,7-dihydrobenzimidazo[1,2-c]quinazolin-6-one derivative according to claim 1, wherein the derivative absorbs electromagnetic radiation in at least one predetermined wavelength subrange of the UV spectral range.

3. The 6,7-dihydrobenzimidazo[1,2-c]quinazolin-6-one derivative according to claim 1, wherein L is CO or $SO_2$.

4. The 6,7-dihydrobenzimidazo[1,2-c]quinazolin-6-one derivative according to claim 1, wherein said derivative has the general structural formula selected from the group comprising structures 1 to 11:

(1)

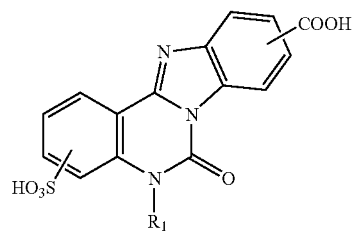

(2)

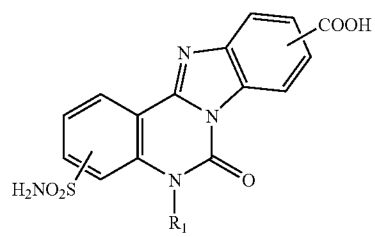

(3)

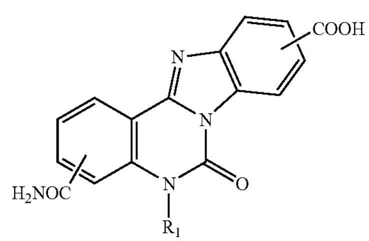

(4)

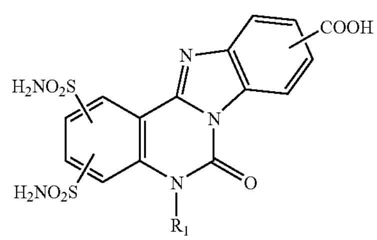

(5)

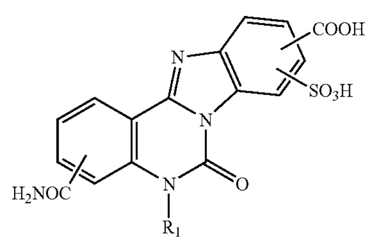

-continued (6)

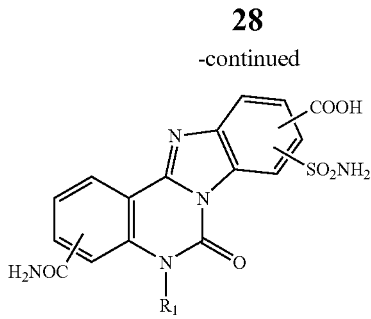

(7)

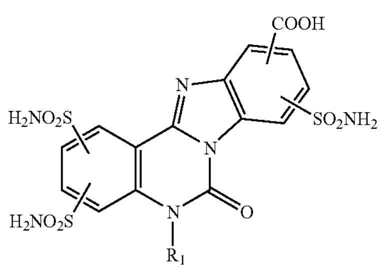

(8)

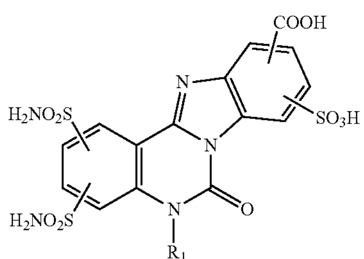

(9)

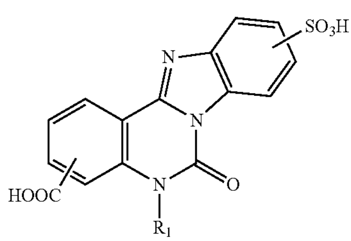

(10)

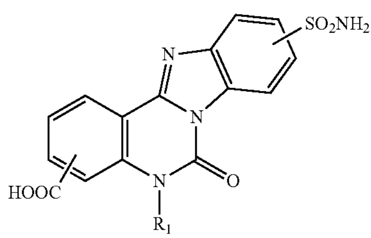

(11)

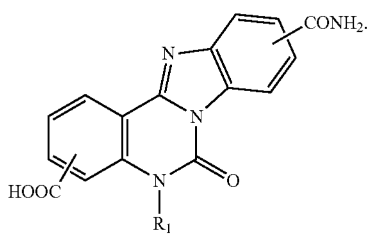

5. The 6,7-dihydrobenzimidazo[1,2-c]quinazolin-6-one derivative according to claim 1, wherein said derivative has the general structural formula selected from the list comprising structures 12 to 20:

-continued (12)

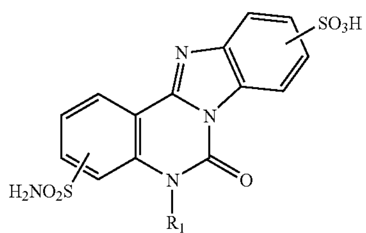

(13)

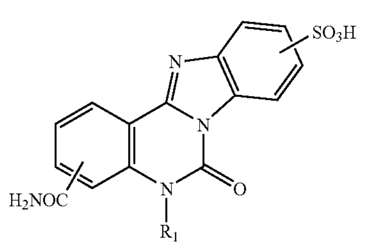

(14)

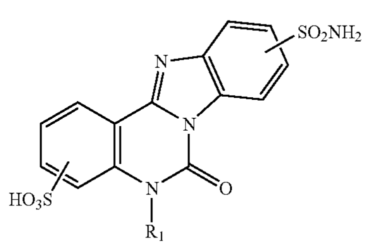

(15)

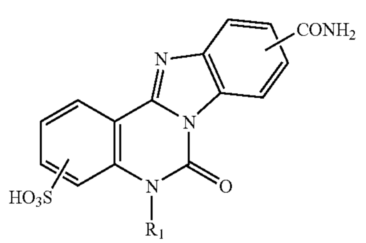

(16)

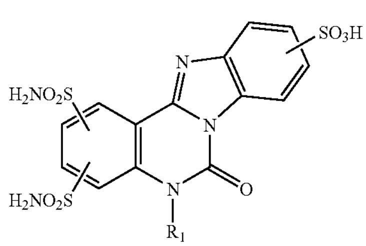

(17)

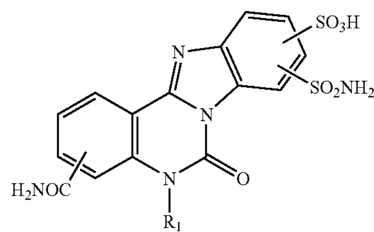

(18)

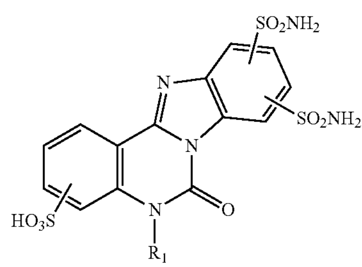

(19)

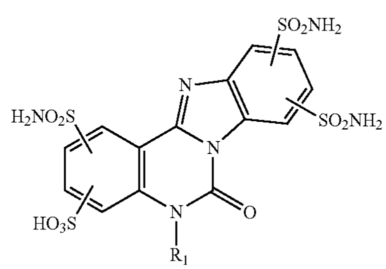

(20)

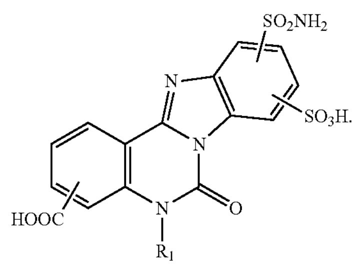

6. The 6,7-dihydrobenzimidazo[1,2-c]quinazolin-6-one derivative according to claim 1 selected from the group consisting of the following compounds:

2(3)-sulfo-6,7-dihydrobenzimidazo[1,2-c]quinazolin-6-one-9-carboxylic acid;

2(3)-sulfo-6,7-dihydrobenzimidazo[1,2-c]quinazolin-6-one-10-carboxylic acid;

2(3)-sulfonamide-6,7-dihydrobenzimidazo[1,2-c]quinazolin-6-one-9-carboxylic acid;

2(3)-sulfonamide-6,7-dihydrobenzimidazo[1,2-c]quinazolin-6-one-10-carboxylic acid;

2(3)-sulfo-6,7-dihydrobenzimidazo[1,2-c]quinazolin-6-one-9-carboxylic acid amide;

2(3)-sulfo-6,7-dihydrobenzimidazo[1,2-c]quinazolin-6-one-10-carboxylic acid amide; and 6,7-dihydrobenzimidazo[1,2-c]quinazolin-6-one sulfo-sulfonamides.

7. An anisotropic optical film comprising a substrate having front and rear surfaces, and at least one organic layer applied onto the front surface of the substrate, wherein the organic layer comprises at least one 6,7-dihydrobenzimidazo[1,2-c]quinazolin-6-one derivative of the general structural formula I

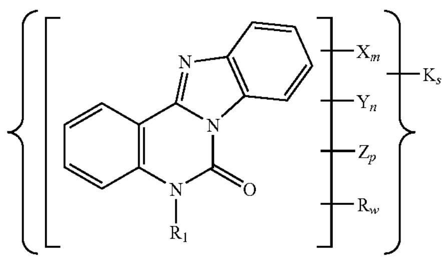

wherein X is a carboxylic group COOH, m is 0, 1, 2, or 3;

Y is a sulfonic group $SO_3H$, n is 0, 1, 2 or 3;

Z is an acid amide group $L\text{-}NH_2$, wherein L is a linking group, p is 0, 1, 2 or 3;

K is a counterion selected from the group consisting of $H^+$, $NH_4^+$, $Na^+$, $K^+$, $Li^+$, $Mg^{2+}$, $Ca^{2+}$, $Zn^{2+}$, and $Al^{3+}$, s is the number of counterions providing neutral state of the molecule;

R is a substituent selected from the group consisting of $CH_3$, $C_2H_5$, $NO_2$, Cl, Br, F, $CF_3$, CN, OH, $OCH_3$, $OC_2H_5$, $OCOCH_3$, OCN, SCN, $NH_2$, and $NHCOCH_3$, w is 0, 1, 2, 3 or 4;

$R_1$ is a substituent selected from the group consisting H, $CH_3$, $C_2H_5$, $C_3H_7$, $i\text{-}C_3H_7$, $CH_2CH_2CH_2CH_3$, $CH(CH_3)CH_2CH_3$, $CH_2CH(CH_3)CH_3$ and $C(CH_3)_3$; and wherein the values of at least two of said integers m, n and p are not equal to 0 and said derivative comprises at least two different groups selected from the list comprising X, Y, and Z; and wherein said organic layer does not substantially absorb incident electromagnetic radiation in the visible spectral range.

8. The anisotropic optical film according to claim 7, wherein the linking group L is CO or $SO_2$.

9. The anisotropic optical film according to claim 7, wherein said at least one organic at least layer provides absorption of electromagnetic radiation in at least one predetermined wavelength subrange of the UV spectral range.

10. The anisotropic optical film according to claim 7, wherein said organic layer is substantially insoluble in water and/or water-miscible solvents.

11. The anisotropic optical film according to claim 7, wherein said organic layer contains two or more different 6,7-dihydrobenzimidazo[1,2-c]quinazolin-6-one derivatives of the general structural formula I, each derivative absorbing electromagnetic radiation in at least one predetermined wavelength subrange of the UV spectral range.

12. An anisotropic optical film according to claim 7, wherein said organic layer is a biaxial retardation layer characterized by two in-plane refractive indices (nx and ny) and one refractive index (nz) in a direction normal to the plane.

13. The anisotropic optical film according to claim 12, wherein the refractive indices nx, ny and nz obey the following condition for electromagnetic radiation in the visible spectral range:

$$nx<ny<nz.$$

14. The anisotropic optical film according to claim 13, wherein the in-plane refractive indices (nx and ny) and the organic layer thickness d obey the following condition:

ti $d\cdot(ny-nx)<20$ nm.

15. The anisotropic optical film according to claim 12, wherein the refractive indices nx, ny and nz obey the following condition for electromagnetic radiation in the visible spectral range:

$$nx<nz<ny.$$

16. The anisotropic optical film according to claim 15, wherein the refractive indices ny and nz and the organic layer thickness d obey the following condition:

$$d\cdot(ny-nz)<20 \text{ nm}.$$

17. The anisotropic optical film according to claim 7, wherein the substrate comprises a polymer.

18. The anisotropic optical film according to claim 7, wherein the substrate comprises a glass.

19. The anisotropic optical film according to claim 7, wherein the the substrate's transmission coefficient in the UV spectral range does not exceed 2%.

20. The anisotropic optical film according to claim 7, wherein the substrate is transparent for electromagnetic radiation in the visible spectral range.

21. The anisotropic optical film according to claim 20, wherein the substrate's transmission coefficient in the visible spectral range is no less than 90%.

22. The anisotropic optical film according to claim 7, wherein the rear surface of the substrate is covered with an additional antireflection or antiglare coating.

23. The anisotropic optical film according to claim 7, further comprising a reflective layer applied onto the rear surface of the substrate.

24. The anisotropic optical film according to claim 7, wherein the substrate is a specular or diffusive reflector.

25. The anisotropic optical film according to claim 7, wherein the substrate is a reflective polarizer.

26. The anisotropic optical film according to claim 7, further comprising a planarization layer applied onto the front surface of the substrate.

27. The anisotropic optical film according to claim 7, further comprising an additional transparent adhesive layer applied on top of the organic layer.

28. The anisotropic optical film according to claim 27, further comprising a protective coating applied on the transparent adhesive layer.

29. The anisotropic optical film according to claim 27, wherein the transparent adhesive layer's transmission coefficient in the UV spectral range does not exceed 2%.

30. The anisotropic optical film according to claim 27, wherein the transparent adhesive layer's transmission coefficient in the visible spectral range is no less than 90%.

31. The anisotropic optical film according to claim 7, said film comprising two or more organic layers containing different 6,7-dihydrobenzimidazo[1,2-c]quinazolin-6-one derivatives with the general structural formula I, each derivative absorbing of electromagnetic radiation in at least one predetermined wavelength subrange of the UV spectral range.

32. The anisotropic optical film according to claim 7, wherein the 6,7-dihydrobenzimidazo[1,2-c]quinazolin-6-one derivative has the general structural formula selected from the group consisting of structures 1 to 11:

-continued
(1)
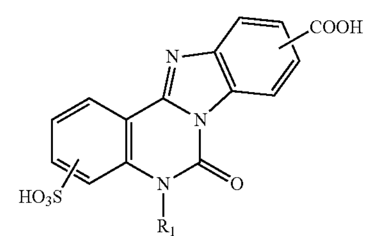
(2)
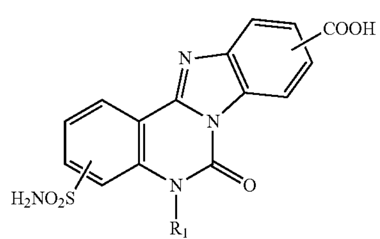
(3)
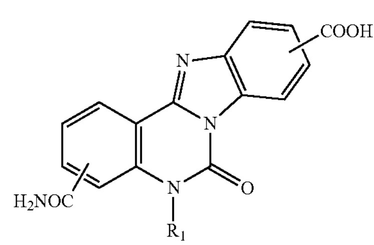
(4)
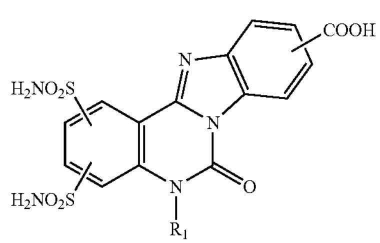
(5)
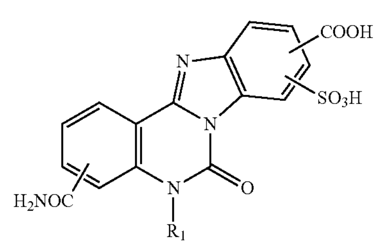
(6)
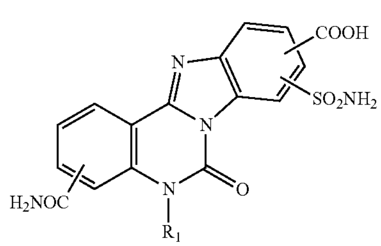
(7)
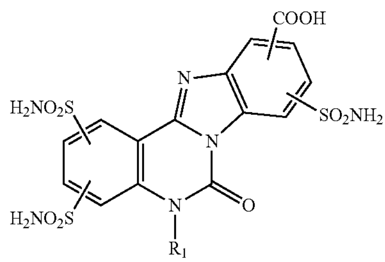
(8)
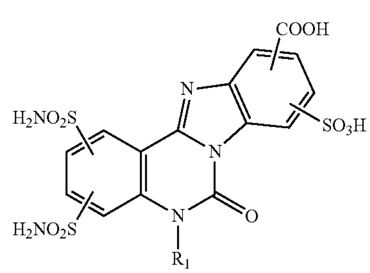
(9)
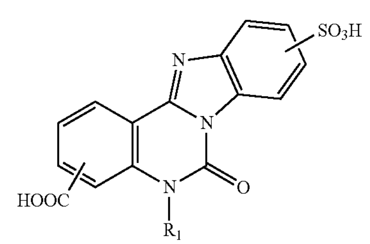
(10)
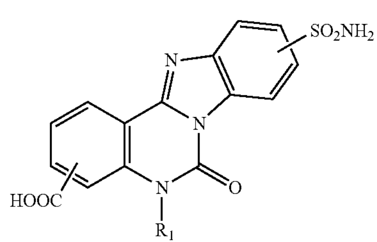
(11)
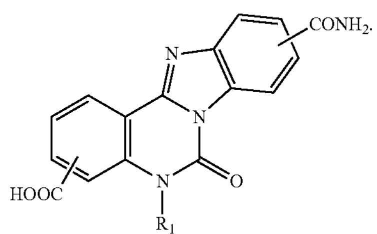
33. The anisotropic optical film according to claim 7, wherein said 6,7-dihydrobenzimidazo[1,2-c]quinazolin-6-one derivative has the general structural formula selected from the group consisting of structures 12 to 20:

(12)

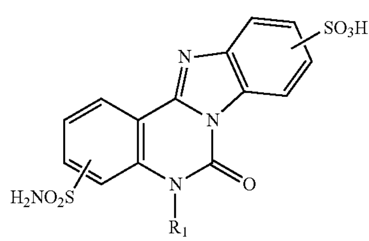

(13)

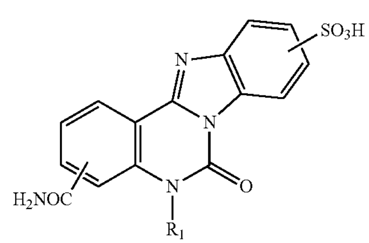

(14)

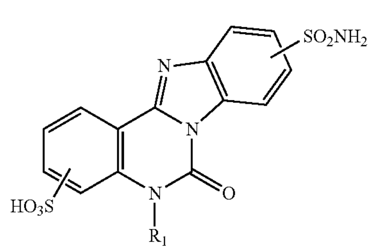

(15)

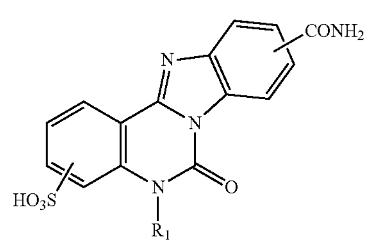

(16)

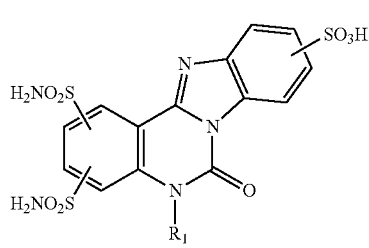

(17)

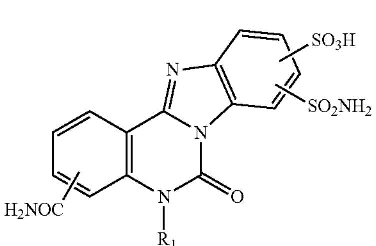

-continued (18)

(19)

(20)

34. The anisotropic optical film according to claim 7, wherein the 6,7-dihydrobenzimidazo[1,2-c]quinazolin-6-one derivative is selected from the group consisting of the following compounds:

2(3)-sulfo-6,7-dihydrobenzimidazo[1,2-c]quinazolin-6-one-9-carboxylic acid;

2(3)-sulfo-6,7-dihydrobenzimidazo[1,2-c]quinazolin-6-one-10-carboxylic acid;

2(3)-sulfonamide-6,7-dihydrobenzimidazo[1,2-c]quinazolin-6-one-9-carboxylic acid;

2(3)-sulfonamide-6,7-dihydrobenzimidazo[1,2-c]quinazolin-6-one-10-carboxylic acid;

2(3)-sulfo-6,7-dihydrobenzimidazo[1,2-c]quinazolin-6-one-9-carboxylic acid amide;

2(3)-sulfo-6,7-dihydrobenzimidazo[1,2-c]quinazolin-6-one-10-carboxylic acid amide; and 6,7-dihydrobenzimidazo[1,2-c]quinazolin-6-one sulfo-sulfonamides.

35. A method of producing an anisotropic optical film comprising the following steps:

(a) depositing an aqueous solution of supramolecules, formed from one or more 6,7-dihydrobenzimidazo[1,2-c]quinazolin-6-one derivatives on a substrate, and (b) drying of said aqueous solution of supramolecules to form a solid layer, wherein said 6,7-dihydrobenzimidazo[1,2-c]quinazolin-6-one derivatives have the general structural formula I

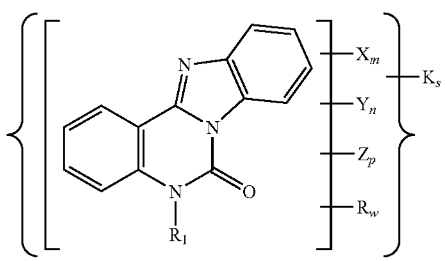

wherein X is a carboxylic group COOH, m is 0, 1, 2 or 3;

Y is a sulfonic group $SO_3H$, n is 0, 1, 2 or 3;

Z is an acid amide group $L\text{-}NH_2$, wherein L is a linking group, p is 0, 1, 2, or3;

K is a counterion selected from the list comprising $H^+$, $NH_4^+$, $Na^+$, $K^+$, $Li^+$, $Mg^{2+}$, $Ca^{2+}$, $Zn^{2+}$, and $Al^{3+}$, s is the number of counterions providing neutral state of the molecule;

R is a substituent selected from the list comprising $CH_3$, $C_2H_5$, $NO_2$, Cl, Br, F, $CF_3$, CN, OH, $OCH_3$, $OC_2H_5$, $OCOCH_3$, OCN, SCN, $NH_2$, and $NHCOCH_3$, w is 0, 1, 2, 3 or 4;

$R_1$ is a substituent selected from the list comprising H, $CH_3$, $C_2H_5$, $C_3H_7$, i-$C_3H_7$, $CH_2CH_2CH_2CH_3$, $CH(CH_3)CH_2CH_3$, $CH_2CH(CH_3)CH_3$ and $C(CH_3)_3$; and wherein the values of at least two of said integers m, n and p are not equal to 0 and said derivative comprises at least two different groups selected from the list comprising X, Y, and Z.

36. The method according to claim 35, further comprising application of an external alignment action to the aqueous solution of supramolecules prior to the drying step.

37. The method according to claim 35, wherein said aqueous solution of supramolecules absorbs electromagnetic radiation in at least one predetermined wavelength subrange of the UV spectral range.

38. The method according to claim 35, wherein the linking group L is CO or $SO_2$.

39. The method according to claim 35, wherein the 6,7-dihydrobenzimidazo[1,2-c]quinazolin-6-one derivative is selected from the group consisting of the following compounds:

2(3)-sulfo-6,7-dihydrobenzimidazo[1,2-c]quinazolin-6-one-9-carboxylic acid;

2(3)-sulfo-6,7-dihydrobenzimidazo[1,2-c]quinazolin-6-one-10-carboxylic acid;

2(3)-sulfonamide-6,7-dihydrobenzimidazo[1,2-c]quinazolin-6-one-9-carboxylic acid;

2(3)-sulfonamide-6,7-dihydrobenzimidazo[1,2-c]quinazolin-6-one-10-carboxylic acid;

2(3)-sulfo-6,7-dihydrobenzimidazo[1,2-c]quinazolin-6-one-9-carboxylic acid amide;

2(3)-sulfo-6,7-dihydrobenzimidazo[1,2-c]quinazolin-6-one-10-carboxylic acid amide; and 6,7-dihydrobenzimidazo[1,2-c]quinazolin-6-one sulfosulfonamides.

40. The method according to claim 35, wherein the drying step comprises treatment with airflow.

41. A method according to claim 40, wherein the drying step is performed at an elevated temperature of 23 to 60 degrees centigrade.

42. A method according to claim 35, wherein the substrate prior to the application of said aqueous solution of supramolecules is pretreated so as to render its surface hydrophilic.

43. A method according to claim 35, further comprising treatment of said formed solid layer with a solution of a water-soluble inorganic salt with $Ba^{2+}$ cation.

44. A method according to claim 35, wherein said aqueous solution of supramolecules has a concentration selected from the range between 1% and 35% to produce the anisotropic optical film having the predetermined properties.

45. A method according to claim 35, wherein said aqueous solution of supramolecules is a lyotropic liquid crystal solution.

46. A method according to claim 35, wherein said aqueous solution of supramolecules is a gel solution.

47. The method according to claim 35, wherein the sequence of technological operations a) and b) are repeated two or more times and the aqueous solution of supramolecules used in the fabrication of each subsequent solid layer is either the same or different from that used in the previous cycle.

48. The method according to claim 35, wherein the 6,7-dihydrobenzimidazo[1,2-c]quinazolin-6-one derivative has the general structural formula selected from the group consisting of structures 1 to 11:

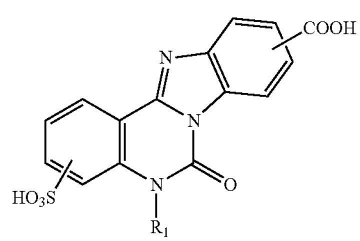

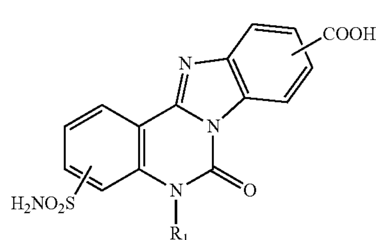

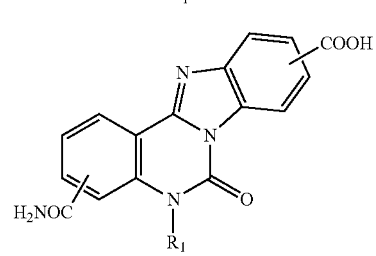

-continued
(4)
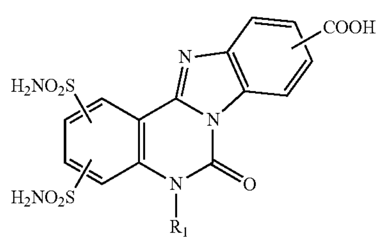
(5)
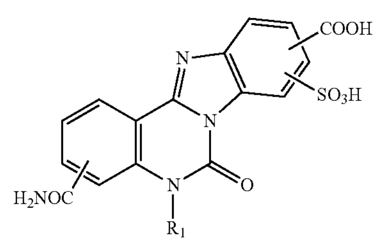
(6)
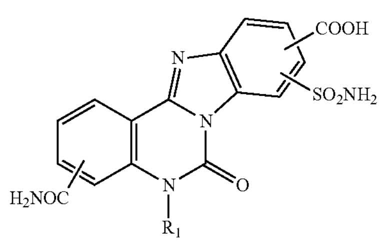
(7)
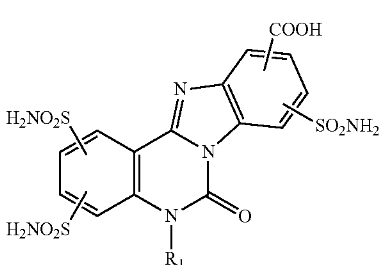
(8)
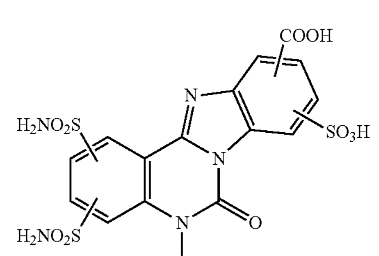
(9)
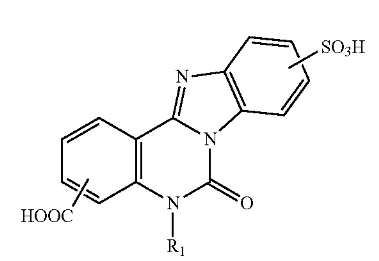
-continued
(10)
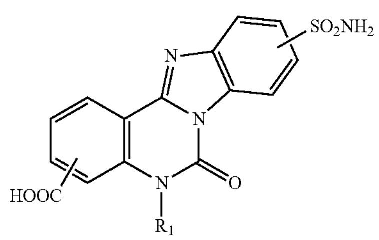
(11)
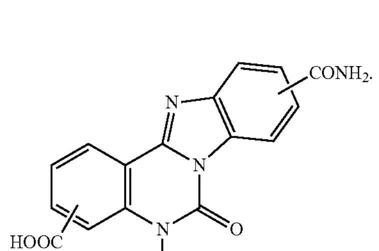
49. The method according to claim 35, wherein said 6,7-dihydrobenzimidazo[1,2-c]quinazolin-6-one derivative has the general structural formula selected from the group consisting of structures 12 to 20:
(12)
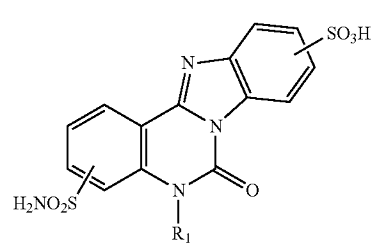
(13)
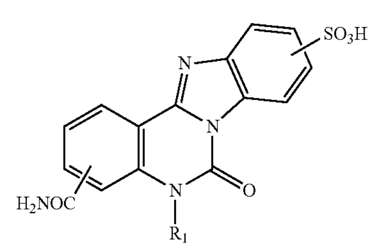
(14)
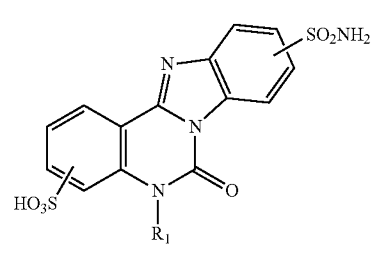

-continued
(15)
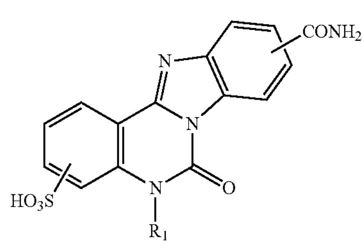
(16)
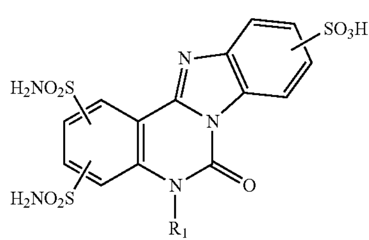
(17)
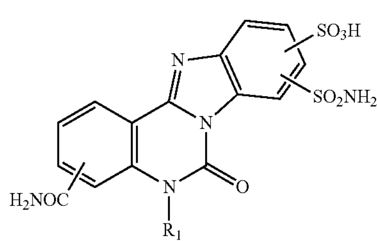
-continued
(18)
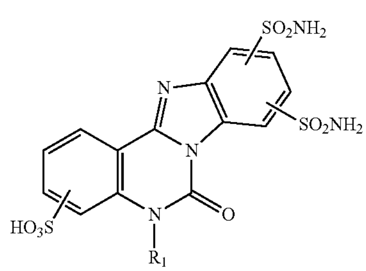
(19)
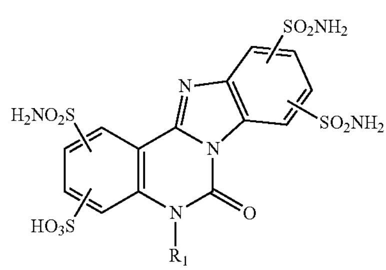
(20)
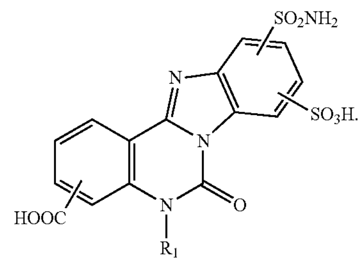
* * * * *

UNITED STATES PATENT AND TRADEMARK OFFICE

CERTIFICATE OF CORRECTION

PATENT NO. : 8,865,895 B2
APPLICATION NO. : 12/160404
DATED : October 21, 2014
INVENTOR(S) : Doutova et al.

It is certified that error appears in the above-identified patent and that said Letters Patent is hereby corrected as shown below:

In the Claims,

Claim 1

Column 26, line 61, “comprising” should be changed to --consisting of--.

Claim 4

Column 27, lines 7-8, “comprising” should be changed to --consisting of--.

Claim 5

Column 28, lines 66-67, “comprising” should be changed to --consisting of--.

Claim 7

Column 31, line 32, after “consisting” insert --of--.
Column 31, line 38, “comprising” should be changed to --consisting of--.

Claim 14

Column 32, line 4, delete “ti” at beginning of line.

Claim 19

Column 32, line 22, delete extra “the” after “the”.

Claim 35

Column 37, line 21, “or3” should be changed to --or 3--.
Column 37, line 22, “comprising” should be changed to --consisting of--.
Column 37, line 27, “comprising” should be changed to --consisting of--.
Column 37, line 31, “comprising” should be changed to --consisting of--.
Column 37, line 38, “comprising” should be changed to --consisting of--.

Signed and Sealed this
Seventeenth Day of February, 2015

Michelle K. Lee
*Deputy Director of the United States Patent and Trademark Office*